(12) United States Patent
Soukka et al.

(10) Patent No.: US 8,182,988 B2
(45) Date of Patent: May 22, 2012

(54) HOMOGENEOUS LUMINESCENCE BIOASSAY

(75) Inventors: Tero Soukka, Turku (FI); Urpo Lamminmäki, Vanhalinna (FI)

(73) Assignee: Hidex Oy, Turku (FI)

( * ) Notice: Subject to any disclaimer, the term of this patent is extended or adjusted under 35 U.S.C. 154(b) by 324 days.

(21) Appl. No.: 12/527,490

(22) PCT Filed: Feb. 26, 2008

(86) PCT No.: PCT/FI2008/050088
§ 371 (c)(1),
(2), (4) Date: Aug. 17, 2009

(87) PCT Pub. No.: WO2008/104638
PCT Pub. Date: Sep. 4, 2008

(65) Prior Publication Data
US 2010/0086930 A1 Apr. 8, 2010

Related U.S. Application Data

(60) Provisional application No. 60/903,514, filed on Feb. 27, 2007.

(30) Foreign Application Priority Data

Feb. 27, 2007 (FI) ...................... 20070163

(51) Int. Cl.
*C12Q 1/68* (2006.01)

(52) U.S. Cl. ...................... 435/6.1; 435/6.11

(58) Field of Classification Search .................. None
See application file for complete search history.

(56) References Cited

U.S. PATENT DOCUMENTS

| 6,768,000 | B1 | 7/2004 | Nardone |
| 2002/0025540 | A1 | 2/2002 | Roberts et al. |
| 2007/0077588 | A1 | 4/2007 | Will |

FOREIGN PATENT DOCUMENTS

| EP | 1 067 134 | 1/2001 |
| WO | WO 98/43072 | 10/1998 |
| WO | WO 00/06778 | 2/2000 |
| WO | WO 02/085667 | 10/2002 |
| WO | WO 03/000933 | 1/2003 |
| WO | WO 2004/046339 | 6/2004 |
| WO | WO 2005/007119 | 1/2005 |
| WO | WO 2007/060280 | 5/2007 |

*Primary Examiner* — Young J Kim
(74) *Attorney, Agent, or Firm* — James C. Lydon

(57) ABSTRACT

A homogenous bioassay including i) a first group containing a short lifetime fluorescent acceptor, and ii) a second group containing a quencher, with the first and second groups linked by at least a first linkage. The bioassay measures the acceptor's fluorescence increase resulting from cleavage of the first linkage and also includes iii) a third group containing a donor for energy transfer to the acceptor, where the donor is an up-conversion fluorescent compound, a long-lifetime fluorescent compound or an electrogenerated luminescent compound. A conformational or terminal epitope is created on the first group through linkage cleavage, and the third group includes a binder with affinity for this epitope. The acceptor's fluorescence is caused by exciting the donor. Also disclosed are bioassay kits for this method.

25 Claims, 9 Drawing Sheets

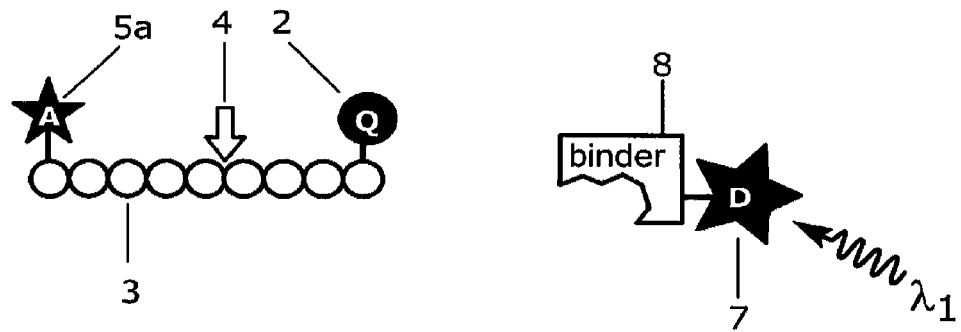
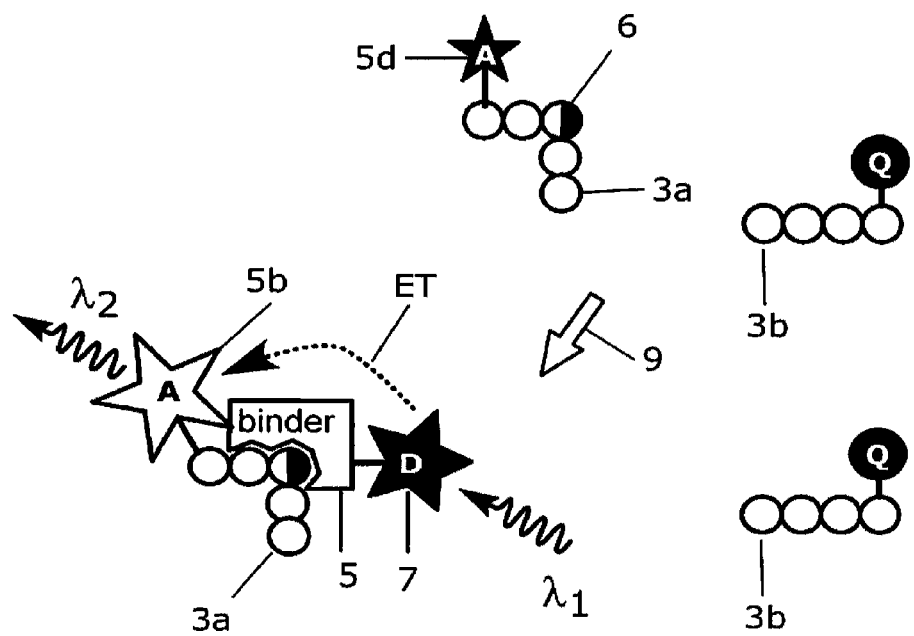
Fig. 6a
Fig. 6b

[Ca²⁺] high        Fig. 8a

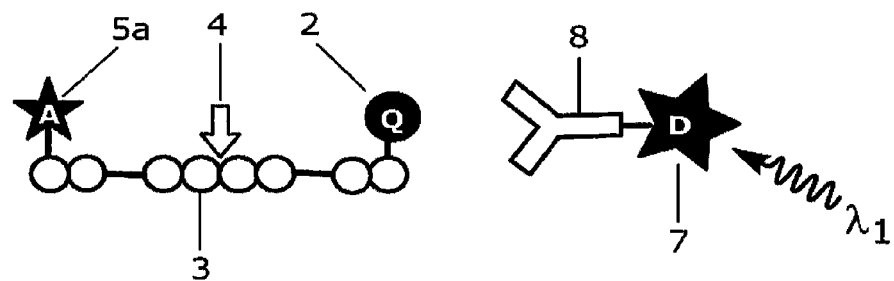
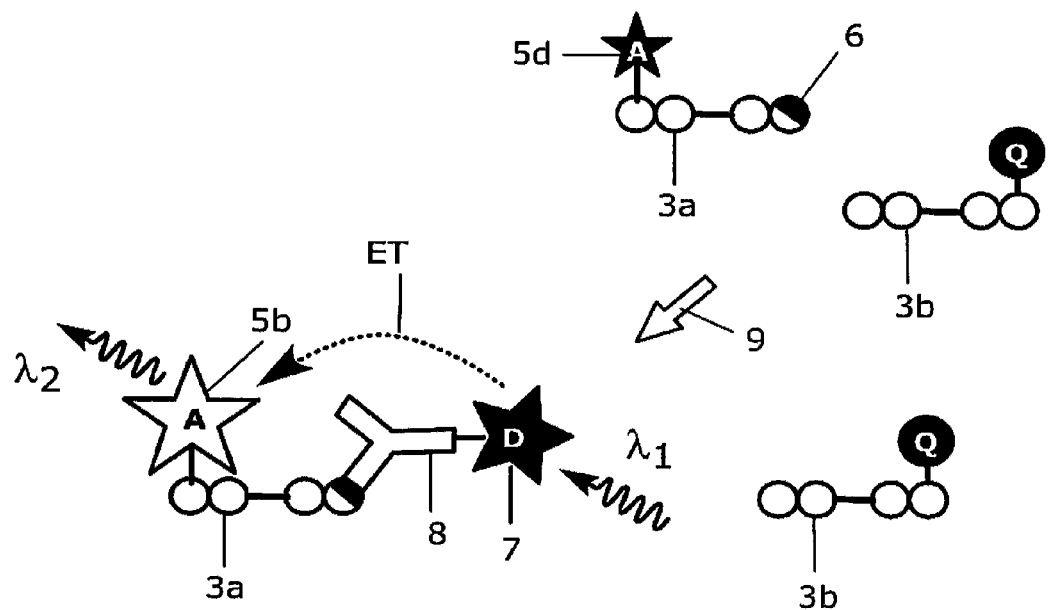
Fig. 9a
Fig. 9b

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: derived from "Swedish Mutant" of amyloid
      protein precursor

<400> SEQUENCE: 1

Cys Glu Val Asn Leu Asp Ala Glu Phe Arg His Asp Ser Gly Lys
1               5                   10                  15

HOMOGENEOUS LUMINESCENCE BIOASSAY

This application is a National Stage of International Application PCT/FI2008/050088, filed Feb. 26, 2008, which claims benefit under 35 U.S.C. §119 of U.S. provisional application 60/903,514, filed Feb. 27, 2007, and Finnish patent application 20070163, filed Feb. 27, 2007.

FIELD OF THE INVENTION

This invention relates to measurement of biological activity or its modulation or analyte concentration using a luminescence energy transfer based homogeneous bioassay.

BACKGROUND OF THE INVENTION

The publications and other materials used herein to illuminate the background of the invention, and in particular, cases to provide additional details respecting the practice, are incorporated by reference.

A number of assays based on bioaffinity binding reactions or enzymatically catalyzed reactions have been developed to analyze biologically important compounds or their activity or their biological effect or its modulation from various biological samples (such as serum, blood, plasma, saliva, urine, faeces, seminal plasma, sweat, liquor, amniotic fluid, tissue homogenate, ascites, etc.), samples in environmental studies (waste water, soil samples), industrial processes (process solutions, products) and compound libraries (screening libraries which may comprise organic compounds, inorganic compounds, natural products, extracts of biological sources, biological proteins, peptides, or nucleotides, etc.). Some of these assays rely on specific bioaffinity recognition reactions, where generally natural biological binding components are used to form the specific binding assay (with biological binding components such as antibodies, natural hormone binding proteins, peptides, lectins, enzymes, receptors, single and double-stranded nucleic acids) or artificially produced binding compounds like aptamers, artificial nucleic acid mimics, genetically or chemically engineered antibodies (Lipovsek D, Pluckthun A. In-vitro protein evolution by ribosome display and mRNA display. *J Immunol Methods.* 2004; 290: 51-67; Pini A, Bracci L. Phage display of antibody fragments. *Curr Protein Pept Sci.* 2000; 1: 155-169; and Hoogenboom H R. Overview of antibody phage-display technology and its applications. *Methods Mol Biol.* 2002; 178: 1-37), moulded plastic imprint (molecular imprinting), other assays rely on activity or modulation of the activity of compounds present in sample or added into reaction (e.g. biologically active enzymes, chemical compounds with activity on biological molecules, enzyme substrates, enzyme activators, enzyme inhibitors, enzyme modulating compounds) and so on. Such assays generally rely on a label or a combination of multiple labels generating signals to quantitate the formed complexes after recognition and binding reaction. In heterogeneous assays a separation step (separations like precipitation and centrifugation, filtration, affinity collection to e.g. plastic surfaces such as coated assay tubes, slides or microparticles, solvent extraction, gel filtration, or other chromatographic systems, and so on) is generally required before e.g. the free or bound fraction of the label signal can be measured. In homogeneous assays the signal of the label or labels is modulated due to binding reaction or enzymatic activity or other measured effect and no separation step is needed before measurement of the label signal. Both in heterogeneous and homogeneous assays the measurement of the label signal from free or bound fraction of the label generally enables the calculation of the analyte or activity in the sample directly or indirectly, generally through use of a set of standards to which unknown samples are compared. Different binding assay methods have been reviewed recently in Principles and Practice of Immunoassay, 2nd ed., C. P. Price and D. J. Newman, eds., Palgrave Macmillan, Hampshire, UK, 2001; and The Immunoassay Handbook, 2nd ed. David Wild, ed., Nature Publishing Group, New York, N.Y., 2001.

Binders for Peptides and Polypeptides

Various types of proteins recognizing specific terminal peptide sequences can be produced artificially. Specific polyclonal and monoclonal antibodies (Köhler and Milstein, *Nature* (1975) 256: 495-497) against a wide range of chemical structures, including terminal sequences of peptides/polypeptides as well as specific peptide/polypeptide conformations, can be raised by immunizing mice or various other animals with suitable antigens. An example of a terminal sequence specific antibody is the monoclonal mouse antibody M1 raised against FLAG-Tag (DYKDDDDK) peptide epitope. In the presence of bivalent cation (preferably calcium), antibody M1 specifically binds to free N-terminus of the FLAG-peptide with high affinity, but has does not recognize the FLAG-peptide if there are one or more additional amino acids in the N-terminus of the peptide (Pricett et al., Bio Techniques (1989) 7: 580-589). The antibody MFS, in turn, is able to recognize a divalent cation-induced conformational change in myosin light chain 2 (Reinach and Fischman, *J. Mol. Biol.* (1985) 81:411-22).

Antibodies against terminal sequences or specific protein conformations can also be developed by selecting them from recombinant antibodies libraries (see e.g., Marks, et al., *J. Mol. Biol.* (1991) 222, 581-97., Knappik, et al., *J. Mol. Biol.* (2000) 296, 57-86; Söderlind, et al., *Nat. Biotechnol.* (2000) 18, 852-6) using, for example, phage display technique (Smith, Science 228 (2005), 1315-7). For example, recombinant antibody phage libraries were employed for development of the recombinant antibody Fab-fragment H2 which exclusively binds to active Ras protein, and not to inactive Ras (Horn et al., *FEBS Lett.* (1999) 463:115-20). Currently, several other protein frameworks (scaffolds) in addition to antibodies have been recruited for the development of recombinant protein binders against various targets. The binders based on scaffold proteins include, for example, anticalins (based on lipocalin structures; Skerra, *Rev. Mol. Biotechnol,* (2001) 74: 257-275), trinectins (derived from a fibronectin III domain; Xu et al., *Chem. Biol.* (2002) 9: 933-942), and affibody molecules (engineered from the Z domain of protein A; Nord et al., *Nat. Biotechnol.,* (1997), 15: 772-777) as well as DARPins (designed on ankyrin repeat protein framework: Binz et al *Nat. Biotechnol.* (2004) 22:575-82). More examples of the scaffolds can be found, for example, in the review article by Binz and Pluckthun (*Curr. Opin. Biotechnol.* (2005) 16: 459-469). The scaffold protein based binder libraries can be subjected for selections and screening procedures in order to develop binders against terminal sequences or conformational epitopes in peptides and polypeptides. It is likely that in the future yet another protein folds will be recruited for development of binder molecules. It is also possible to generate completely new proteins folds with specific binding activities using, for example, by exon shuffling approach (Riechmann and Winter, *Proc Natl Acad Sci USA.* (2000) 97: 10068-73). Owing to the progress in the field of computer-assisted structural modelling of proteins, it has become possible to produce specific binder proteins against various targets by designing binding sites in silico into a suitable framework structure followed by introduction of the corresponding mutations in practice. (Looge et al., Nature (2003) 423:185-90). Various protein folds can act as a framework for in silico design approaches.

A large number of natural proteins interact with each other in a conformation specific manner. For example, spectrin EF-hands undergo a major conformational change upon calcium binding from a 'closed' to an 'open' state allowing protein-protein interaction (Trave et al., *EMBO J.* (1995) 14:4922-31). Again, several natural proteins specifically recognize terminal peptide sequences (either N- or C-terminal) in other proteins. These proteins or their domains responsible for the binding provide a potential source of binder molecules for recognition of specific conformation or terminal peptide segments. PDZ domain and PYX, for example, are specialized for recognition of C-terminal peptide sequences (Chung et al., (2002) *Trends Cell Biol.* 12:146-50). Another protein type binding to C-terminal sequences are known as 14-3-3 proteins, which can bind to specific phosphorylated C-terminal sequences (Coblitz, et al. *FEBS Lett.* (2006) 580:1531-5). N-terminal sequences in endogenous proteins are, in turn, specifically recognized by certain N-end rule pathway related proteins as a part of a process targeting proteins for degradation. In prokaryotes, ClpS protein binds to the degradation signal that comprises N-terminal destabilizing residues (Erbse et al., *Nature* (2006) 439:753-6), while, in eukaryotes, the N-terminal degradation signal of the N-end rule is recognized by N-recognin proteins (Varhaysky, *Proc. Natl. Acad. Sci.* (1996) 93, 12142-12149). If necessary, various mutagenesis methods can be employed for modulation of the binding properties (such as the specificity and affinity) of terminal peptide recognizing natural proteins (see, for example, Skelton et al., *J Biol. Chem.* (2003) 278:7645-54).

Aptamers are nucleic acids based binder molecules, which primarily consist of natural nucleic acids (DNA and RNA) and can also contain artificially introduced chemical moieties such as non-natural nucleotides. Specific aptamers against various target molecules can be systematically produced by using, for example, a technique called systematic evolution of ligands by exponential enrichment (SELEX; Tuerk and Gold, *Science* (1990) 249: 505-510), where nucleic acid molecules are, first, selected for binding to target and then amplified by using an enzymatic reaction. Until today, specific aptamers have been developed for a wide array of target molecules ranging from small molecular compounds to large macromolecules such as proteins (Proske, et al., *Appl Microbiol Biotechnol.* (2005) 69:367-74), and it should be possible to produce aptamers that specifically bind either to N- or C-terminal peptide sequences or to specific peptide/polypeptide conformations. For example, aptamers that bind selectively to $PrP^C$ form of the prion protein and not $PrP^{Sc}$ form have been developed (Takemura et al., *Exp Biol Med* (Maywood) (2006). 231:204-14).

Binders for Carbohydrates

Specific antibodies against various carbohydrate structures can be produced by immunization or by selecting/screening binders from recombinant antibody libraries (see, for example, Sakai et al., *Biochemistry* (2007) 46:253-62). Various scaffold proteins based libraries as well as aptamer libraries (Masud at al, *Bioorg Med. Chem.* (2004) 12:1111-20) can also be employed for the development of carbohydrate binders. In addition to the artificially developed binders, there are a number a natural proteins that have capability to recognize and bind specific carbohydrate structures. For example, lectins form a diverse group of proteins that have in common their ability to specifically recognize certain carbohydrates (Loris., *Biochim Biophys Acta*. (2002) 1572:198-208). Some lectins show discrimination between different terminal structures of carbohydrates (see, for example, Hirabayashi et al., *Biochim Biophys Acta*. (2002) 1572:232-54). The binding properties of the natural carbohydrate binder proteins can be modulated by means of protein engineering (Yabe et al., *J Biochem* (Tokyo) (2007) Epub ahead of print).

Binders for Nucleic Acids

The capability of a nucleic acid segment to specifically hybridize to another nucleic acid segment with complementary sequence is widely employed for detection of nucleic acid sequences of interest. The single stranded nucleic acid probes used for detection of a target nucleic acid sequence can be based either on natural nucleic acids, DNA or RNA, and their chemically modified derivatives as well as on artificial nucleic acid analogues such as peptide nucleic acids (PNA), locked nucleic acids (LNA) or morpholinos (Karkare and Bhatnagar, *Appl Microbiol Biotechnol*. (2006) 71:575-86). DNA has also property to form triple helix structures: A third DNA strand can bind into the major groove of a homopurine duplex DNA to form a DNA triple helix, and this property can also be utilized for specific recognition of DNA sequences (see, for example, Ji et al., *Genomics* (1996) 31:185-92). Antibodies (Di Pietro et al., *Biochemistry* (2003) 42:6218-27) and apparently various scaffold protein as well as aptamers can also be utilized for specific recognition of DNA segments.

Fluorescence Resonance Energy Transfer

Fluorescence resonance energy transfer (FRET) (Förster, T. Intermolecular energy migration and fluorescence. Ann. Physik 1948; 2, 55-75.) (or Förster resonance energy transfer) describes an energy transfer mechanism between two fluorescent molecules or between a fluorescent and a non-luminescent molecule. A fluorescent donor is excited at its specific fluorescence excitation wavelength. By a long-range dipole-dipole coupling mechanism, this excited state is then nonradiatively transferred to a second molecule, the acceptor, which is luminescent and can emit at its specific emission wavelength, or the quencher, which is non-luminescent or luminescent. The donor returns to the electronic ground state. The mechanism is widely employed in biomedical research (reviewed by Selvin P R The renaissance of fluorescence resonance energy transfer. Nat Struct Biol 2000; 7: 730-734; and Lakowicz, J. Principles of fluorescence spectroscopy, $2^{nd}$ edition. Plenum Press, New York, 1999).

The FRET efficiency is determined by the distance between the donor and the acceptor, the spectral overlap of the donor emission spectrum and the acceptor absorption spectrum, and the relative orientation of the donor emission dipole moment and the acceptor absorption dipole moment. The FRET efficiency E depends on the donor-to-acceptor distance r with an inverse 6th order law defined by $$E=1/(1+(r/R_0)^6)$$

with $R_0$ being the Förster distance of this pair of donor and acceptor at which the energy transfer efficiency is 50%. The Förster distance depends on the overlap integral of the donor emission spectrum with the acceptor absorption spectrum and their mutual molecular orientation.

Self-Quenched Fluorescent Oligomers and Oligomeric Substrates

Bio-oligomer derivatives, for example oligopeptide, oligonucleotide and oligosaccharide derivatives, containing both a fluorescent moiety and a quencher moiety covalently attached typically to different ends of the same oligomer molecule, are employed to measure hydrolysation or cleavage of the oligomer upon for example enzymatic or chemical activity. The hydrolysis and cleavage, resulting in increase in the distance between a fluorescent moiety and a quencher moiety, are accompanied by an increase in the fluorescence due to disruption of the intramolecular quenching of the fluorescent moiety. The spectral properties of the moieties do not necessarily need to be consistent with an energy transfer mechanism according to Förster requiring spectral overlapping between emission spectra of the fluorescent moiety (donor) and excitation spectra of the quencher moiety.

Self-quenched oligopeptide substrates, also called fluorogenic substrates, and their applications have been described e.g. by Lottenberg R, Christensen U, Jackson C M, Coleman P L Assay of coagulation proteases using peptide chromogenic and fluorogenic substrates. *Methods Enzymol.* 1981; 80: 341-61; and by Lew R A, Tochon-Danguy N, Hamilton C A, Stewart K M, Aguilar M I, Smith A L Quenched fluorescent substrate-based peptidase assays. *Methods Mol Biol.* 2005; 298: 143-150. The use of specific quenched fluorescent oligopeptide substrates provides a rapid and sensitive method to measure peptidase activity, and is readily adaptable to high-throughput screening of potential peptidase inhibitors. A high throughput assay based on a peptide labelled with both a fluorescent europium chelate and a quencher has been described by Karvinen J, Hurskainen P, Gopalakrishnan S, Burns D, Warrior U, Hemmila I. Homogeneous time-resolved fluorescence quenching assay (LANCE) for caspase-3. *J Biomol Screen.* 2002; 7: 223-231. The principle of a peptidase assay based on quenched fluorescent substrate is illustrated in FIG. 1. In an intact fluorescent substrate the fluorescent label is quenched by the quencher, but when a peptidase cleaves the substrate the distance between the fluorescent label and the quencher increases recovering the fluorescence of the fluorescent compound. The measured signal is increased upon cleavage of the substrate.

Cleavage of the peptide by caspase-3 separates the quencher from the chelate and thus recovers fluorescence of europium chelate. A similar assay is possible by using a long-lifetime fluorescent metal-porphyrin label (O'Riordan T C, Hynes J, Yashunski D, Ponomarev G V, Papkovsky D B. Homogeneous assays for cellular proteases employing the platinum(II)-coproporphyrin label and time-resolved phosphorescence. *Anal Biochem* 2005; 342: 111-119). Phosphorescent platinum(II) coproporphyrin label was evaluated for the detection of cellular proteases by time-resolved fluorescence in homogeneous format. An octameric peptide containing the recognition motif for the caspase-3 enzyme was dual labelled with a new maleimide derivative of phosphorescent platinum(II) coproporphyrin label and with the non-luminescent quencher dabcyl. Donor-acceptor energy transfer and fluorescence quenching based assays have been described also for other enzymes: a protease related to apoptosis, helicase involved in DNA unwinding, and phosphatase having an important role in cellular signaling cascades (Karvinen J, Laitala V, Makinen M L, Mulari O, Tamminen J, Hermonen J, Hurskainen P, Hemmila I. Fluorescence quenching-based assays for hydrolyzing enzymes. Application of time-resolved fluorometry in assays for caspase, helicase, and phosphatase. *Anal Chem* 2004; 76: 1429-1436).

A cleavage assay can also be constructed using e.g. a terbium-chelate donor labelled streptavidin and using a biotinylated peptide substrate containing dabcyl as non-luminescent quencher or fluorescein as a luminescent acceptor at the other end of the peptide sequence. A similar cleavage assay using europium-chelate and donor labelled biotinylated peptide and streptavidin conjugate of XL665 luminescent acceptor is described in Kennedy M E, Wang W, Song L, Lee J, Zhang L, Wong G, Wang L, Parker E. Measuring human beta-secretase (BACE1) activity using homogeneous time-resolved fluorescence. *Anal Biochem.* 2003; 319: 49-55.

The principle of an assay with non-luminescent quencher is illustrated in FIG. 2, where the intact peptide contains both biotin and quencher moieties and is capable to bind to a fluorescent conjugate of streptavidin and quenches the fluorescence of the fluorescent label. When the peptide is cleaved the biotin and quencher moieties are separated and the quencher label is unable to bind to streptavidin and the fluorescence of the fluorescent label is not affected. Thus, the measured signal is increased upon cleavage of the substrate, because the cleavage prevents the quenching of the fluorescent label. The concentration of the fluorescent conjugate of streptavidin must be carefully adjusted because an excess of it results in a significant increase in the background signal.

FIG. 3 illustrates an assay based on a luminescent acceptor, where the substrate contains both biotin and acceptor moieties and is capable to bind to a donor conjugate of streptavidin. The sensitized acceptor emission is dependent on the proximity of donor and acceptor and only the acceptor present in an intact substrate is able to bind to streptavidin. Upon cleavage of the substrate the measured signal is decreased. The donor conjugate of streptavidin can be used in excess because signal without significant increase in the background signal. This method is used by Invitrogen (Carlsbad, Calif.; www.invitrogen.com) in their Lanthascreen concept based on terbium-chelate labelled streptavidin and biotinylated substrate labelled with fluorescein (http://www.invitrogen.com/-downloads/F-13279_LanthaScreen_Poster.pdf). The time-resolved FRET value is determined as a ratio of the FRET-specific signal measured with a 520 nm filter to that of the signal measured with a 495 nm filter, which is specific to terbium-chelate.

Fluorescence quenching assay based on an electrochemiluminescent label and luminescence quenching based on energy transfer is described in Spehar A M, Koster S, Kulmala S, Verpoorte E, de Rooij N, Koudelka-Hep M. The quenching of electrochemiluminescence upon oligonucleotide hybridization. *Luminescence* 2004; 19: 287-95. Interaction between electrochemically excited $Ru(bpy)_3^{2+}$ and Cy5 in a hybridization assay on a chip was studied. The 3' end of an oligonucleotide was labelled with $Ru(bpy)_3^{2+}$ and the 5' end of a complementary strand with Cy5. Upon the hybridization, the electrochemiluminescence (ECL) of $Ru(bpy)_3^{2+}$ was efficiently quenched by Cy5 with a sensitivity down to 30 nmol/l of the Cy5-labelled complementary strand. The quenching efficiency is calculated to be 78%.

Quantitative 5'-nuclease based polymerase chain reaction assay (TaqMan; Applied Biosystems, Foster City, Calif.) is a nucleic acid sequence detection method wherein a single-stranded self-quenching oligonucleotide probe, containing both a fluorescent moiety and a quencher moiety, is cleaved by the nuclease action of nucleic acid polymerase upon hybridisation during nucleic acid amplification (Lie Y S, Petropoulos C J. Advances in quantitative PCR technology: 5' nuclease assays. *Curr Opin Biotechnol.* 1998; 9: 43-48; and Orlando C, Pinzani P, Pazzagli M. Developments in quantitative PCR. *Clin Chem Lab Med.* 1998; 36: 255-269).

Molecular beacons are single-stranded oligonucleotide hybridization probes that form a stem-and-loop structure (Tan W, Wang K, Drake T J. Molecular beacons. *Curr Opin Chem. Biol.* 2004; 8: 547-553; and Tan W, Fang X, Li J, Liu X. Molecular beacons: a novel DNA probe for nucleic acid and protein studies. *Chemistry* 2000; 6: 1107-1111). The loop contains a nucleic acid probe sequence that is complementary to a target sequence, and the stem is formed by the annealing of complementary arm sequences that are located on either side of the probe sequence. A fluorescent moiety is covalently linked to the end of one arm and a quencher is covalently linked to the end of the other arm. Due to the proximity of a fluorescent moiety and a quencher moiety molecular beacons do not fluoresce when they are free in solution. However, when they hybridize to a complementary nucleic acid strand containing a target sequence they undergo a conformational change increasing the distance between fluorescent moiety and the quencher moiety that enables the probe to fluoresce. In the absence of a complementary target sequence, the beacon probe remains closed and there is no fluorescence due to intramolecular quenching.

Selective cleavage of internucleotide bonds of self-quenched single-stranded oligonucleotide probes, which contain one or more ribonucleotides, by RNase H upon double-stranded helix formation subsequent to hybridisation to target is another method of target sequence detection (Rizzo J, Gifford L K, Zhang X, Gewirtz A M, Lu P. Chimeric RNA-DNA molecular beacon assay for ribonuclease H activity. *Mol Cell Probes* 2002; 16: 277-283). Yet another method is to use a self-quenched single-stranded oligonucleotide cycling probe, which is cleaved by a double-stranded selective exonuclease upon hybridisation to target sequence. Examples of nuclease-based assays are found in e.g. Till B J, Burtner C, Comai L, Henikoff S, *Nucleic Acids Res.* 2004; 32: 2632-2641.

Self-quenched fluorescent probes are also used to monitor nucleic acid amplification process in a thermal cycler; for example in quantitative polymerase chain reaction the amount of fluorescence at any given cycle, or following cycling, depends on the amount of specific product. The self-quenched single-stranded fluorescent probes, for example molecular beacons or Taqman probes, bind to the amplified target following each cycle of amplification and the resulting signal upon hybridisation, and in case of Taqman probes upon cleavage, is proportional to the amount of the amplified oligonucleotide sequence. Fluorescence is measured during each annealing step when the molecular beacon is bound to its complementary target or after elongation step when the Taqman probe is cleaved. The information is then used during quantitative PCR or RT-PCR (reverse transcriptase PCR) experiments to quantify initial copy number of amplified target nucleic acid sequence. For endpoint analysis, PCR or RT-PCR reactions containing molecular beacons can be run on any 96-well thermal cycler and then read in a fluorescence reader.

Fluorescent oligosaccharide substrates and their use in fluorescence quenching assay has been described in Cottaz S, Brasme B and Driguez H, A fluorescence-quenched chitopentaose for the study of endo-chitinases and chitobiosidases. *Eur. J. Biochem.* 2000; 267: 5593-5600.

Non-fluorescent acceptor labels and their use in fluorescence quenching assays with short-lifetime fluorescent dyes have been described e.g. in U.S. Pat. No. 6,828,116.

Ribonuclease detection using dual-labelled quenched fluorescent oligonucleotide containing both short-lifetime fluorescent dye and non-luminescent acceptor has been described in US 2004/0137479.

Fluorescent quenching assay for protein kinase based on fluorescent labelled substrate and phosphate specific binder labelled with non-luminescent acceptor is described in US 2004/024946.

Fluorescence quenching assays based on both fluorescent streptavidin-coated microspheres and conjugates of small-molecule fluorescent dyes in combination with both non-luminescent acceptor dye and quencher polymer have been described in US 2003/0054413.

Fluorescence quenching assay based fluorescent streptavidin-coated microsphere and biotinylated non-luminescent acceptor labelled protease substrate for measurement of protease activity has been described in US 2005/0014160.

Protease activity assay based on dual-labelled fluorescent protein substrate containing binding moiety for purification and separation is described in US 2005/0214890.

In all of the aforementioned examples a fluorescent moiety or a fluorescent compound (donor) is used in combination with either non-luminescent compound (quencher) or luminescent compound (acceptor), respectively, and the donor compound is capable of transferring energy either to a quencher or to an acceptor, respectively, said energy transfer being dependent on the distance between the donor and quencher or acceptor.

In all cases the donor is excited directly by light or electrochemically and, in case of a non-luminescent acceptor, it's the donor's own light emission (fluorescence) is measured or in case of luminescent acceptor, the sensitized emission of an acceptor (originating from energy transfer) is measured.

Advantages of fluorescence quenching based assays and use of quenched fluorogenic substrates to improve the fluorescence-based enzyme assays have been described e.g. by Johansson, M K, Choosing reporter-quencher pairs for efficient quenching through formation of intramolecular dimers. Methods Mol. Biol. 2006; 335: 17-29; and Yang Y, Babiak P and Reymond J L, Low background FRET-substrates for lipases and esterases suitable for high-throughput screening under basic (pH 11) conditions. Org Biomol Chem. 2006; 4: 1746-54.

Homogeneous Bioassay Technologies

Homogeneous assay methods (Ullman E F, *J Chem Ed* 1999; 76: 781-788; Ullman, E F, *J Clin Ligand Assay* 1999; 22: 221-227) based on photoluminescence have received much attention, since several types of physical and chemical interactions can be employed to modulate the emission of photoluminescent labels due to formation of specific immunological complexes. The commonly employed methods are based on polarization of the emitted light or nonradiative energy-transfer between two photoluminescent compounds or between a photoluminescent and a non-luminescent compound (Hemmilä I, *Clin Chem* 1985; 31: 359-370). Fluorescence properties of two fluorescent compounds were employed in a homogeneous immunoassay in late 1970' s when Ullman et al. demonstrated, that fluorescence energy transfer between a fluorescein donor and tetramethylrhodamine acceptor pair could be employed to construct both competitive and non-competitive immunoassays (Ullman E F et al. J Biol Chem 1976; 251: 4172-4178; Ullman E F & Khanna P L, *Methods Enzymol* 1981; 74: 28-60). The energy transfer was measured from decrease in the fluorescence of the donor, which limited further improvements in sensitivity. Increase in the fluorescence of the acceptor was not practicable, since only a little increase in a sensitized acceptor emission could be observed over autofluorescence, light scattering or absorbance of biological sample matrices and the direct emission of the donor at acceptor-specific wavelength.

Many compounds and proteins present in biological fluids or serum are intrinsically fluorescent, and the use of conventional fluorophores leads to serious limitations of sensitivity (Wu P and Brand L, *Anal Biochem* 1994; 218:1-13). Another major problem with homogeneous fluorescence techniques is the inner filter effect and the variability of the optical properties of a sample. Sample dilution has been used to correct this drawback, but always at the expense of analytical sensitivity. Feasibility of fluorescence energy transfer in immunoassays was significantly improved when fluorescent lanthanide cryptates and chelates with long-lifetime emission and large Stokes' shift were employed as donors in the 1990' s (Mathis G, *Clin Chem* 1993; 39: 1953-1959; Selvin P R et al., *Proc Natl Acad Sci USA* 1994; 91: 10024-10028; Stenroos K et al., Cytokine 1998; 10:495-499; WO 98/15830; U.S. Pat. No. 5,998,146; WO 87/07955). Feasibility of the label technology in dissociation reactions, e.g. cleavage assays has also been described (Karvinen J et al., *J Biomol Screen* 2002; 7: 223-231).

Time-resolved fluorescence detection of sensitized emission allowed elimination of autofluorescence (Soini E and Kojola H Time-resolved fluorometer for lanthanide chelates—a new generation of nonisotopic immunoassays. *Clin Chem* 1983; 29: 65-68). Dual signal ratio measurement (U.S. Pat. No. 5,527,684; Mathis, G, *Clin Chem* 1993; 39: 1953-1959) corrected the variability of optical properties of the sample in homogeneous assay. Fluorescence of the compounds and proteins present in biological fluids has a short lifetime and the use of long-lifetime labels combined with time-resolved detection of the sensitized (prolonged lifetime) acceptor emission allowed minimization of the assay background and improved signal to background ratio. The variability of absorption of excitation light at 337 nm was corrected by measuring the emission of the donor at 620 nm and using the ratio of the energy transfer signal at 665 nm and the emission at 620 nm to generate a quantity that is independent of the optical properties of the serum sample. Homogeneous time-resolved FRET based bioaffinity assays using long-lifetime fluorescent nanoparticles have been described in WO 02/044725 and by Kokko L, Sandberg K, Lövgren T and Soukka T, Europium(III) chelate-dyed nanoparticles as donors in a homogeneous proximity-based immunoassay for estradiol *Anal Chim Acta* 2004; 503: 155-162. In the latter publication it is described that multiple lanthanide chelates inside a single particulate can participate simultaneously in energy transfer to a single acceptor. However, still only a small part of the lanthanide chelates inside the entire particulate can participate in an energy transfer to a single acceptor and thus the entire fluorescence of a particulate label cannot be quenched by a single acceptor moiety. The same problem is also encountered when lanthanide chelates are incorporated in a solid phase.

Separation-free assay technologies based on confocal detection of photoluminescent labels bound on particulate carriers have been introduced as an alternative to real homogeneous assays (Saunders G C et al., *Clin Chem* 1985; 31:2020-2023; Frengen J et al., *Clin Chem* 1993; 39:2174-2181; Fulton R J et al., *Clin Chem* 1997; 43:1749-1756). In recent years, the technology has been developed, and some novel carrier-based immunoassays can be considered as homogeneous assays, since they are practically similar to perform (Hänninen P et al., *Nat Biotechnol* 2000; 18:548; U.S. Pat. No. 5,891,738; Schaertl S et al., *J Biomol Screen* 2000; 5:227-238), although the actual signal of the label is not modulated, but the unbound labelled component is spatially excluded from measurement. These assays are otherwise comparable to homogeneous assays, but measurement is relatively slow, since carrier particles have to be either actively scanned or passively diffuse to a focal point, and a signal associated to several carrier particles is required for reliable measurement (Waris M E et al., *Anal Biochem* 2002; 309: 67-74). To avoid sterical hindrance in binding at least one of the labels, preferably both labels of a label-pair should be of small molecular size.

In most of the conventional homogeneous fluorescence assay technologies, the performance has still severe limitations: the sensitivity is limited by interferences from matrix components and optical properties of matrices, e.g. urine, saliva, serum, plasma or whole blood, to fluorescence yield and level of background, and by the attainable degree of fluorescence modulation, e.g. quenching, enhancement, energy transfer or polarization (Hemmilä I, *Clin Chem* 1985; 31: 359-370). In practice, only wavelengths in the range 600 to 1100 nm, or more preferably in the near infrared, in a wavelength range 650 to 950 nm, are practicable when a whole blood sample is employed (Chance B, Photon Migration in Tissues, pp. 206; Kluwer Academic/Plenum Publishers, 1990, New York).

Homogeneous luminescence-based whole-blood assay based on FRET and up-conversion photoluminescence is described in WO 2004/086049. Upconverting phosphors and their application as donors in FRET-based assays is described in WO 98/43072. Both the excitation and the measurement of sensitized acceptor emission have to be performed at far-red and infrared wavelengths where the sample is transparent, in this case at wavelengths 900-1000 nm and approximately 580-640 or 690-750 nm. Upconversion-FRET based assay performed in whole blood has been described by Kuningas K, Pakkila H, Ukonaho T, Rantanen T, Lovgren T and Soukka T., Upconversion fluorescence enables homogeneous immunoassay in whole blood. Clin Chem. 2007; 53:145-146.

U.S. Pat. No. 6,037,130 describes wavelength shifting probes comprising two conventional fluorescent molecules, which are both covalently attached to the probe, and a quencher, wherein energy-transfer excited emission of the second fluorescent molecule upon excitation of the first fluorescent molecule is measured.

US 2005/0170442 describes the use of a cleavable acceptor and biotin labelled peptide, a cleavage reaction inhibited by phosphorylation of a peptide, and an assay method based on energy transfer from streptavidin labelled with donor to the acceptor in presence of phosphorylation.

FRET-based hybridization assays utilizing multiple donors and donor-to-donor energy transfer are described in EP1067134; both donor and acceptor labelled oligonucleotides hybridize to third complementary target oligonucleotide enabling energy transfer from donor to acceptor. In the reaction mixture, a fourth quencher labelled oligonucleotide, complementary to acceptor labelled oligonucleotide, can be present.

Dual-FRET-probe based assay concept is described in WO 03/000933; in this application two molecular beacon-type quenched probes (one containing donor and quencher, the other acceptor and quencher) are hybridized next to each other to third complementary target oligonucleotide and energy transfer between donor and acceptor is enabled.

Hairpin-forming oligonucleotide probe or primer can be labelled with donor and acceptor (energy transfer pair) as well as quencher as described in WO 00/06778, U.S. Pat. No. 6,768,000 and also in US 2007/0077588. In the presence of a second complementary target oligonucleotide the distance between acceptor and quencher is increased, which enables energy-transfer excited acceptor emission.

Formation of a FRET-pair through ligation of two oligonucleotide probes, one labelled with donor and the other with acceptor, is described by Abe H and Kool ET (2006), Flow cytometric detection of specific RNAs in native human cells with quenched autoligating FRET probes, Proc Natl Acad Sci USA, 103: 263-8.

OBJECT AND SUMMARY OF THE INVENTION

One object of the present invention is to provide a homogenous bioassay for use in measurement of biological activity, its modulation or analyte concentration of a sample.

Another object of the present invention is to provide a kit for a homogenous bioassay according to invention.

The present invention provides a homogenous bioassay comprising i) a first group comprising an acceptor, which acceptor is a short lifetime fluorescent compound capable of energy transfer, and ii) a second group comprising a quencher, which quencher is capable of energy transfer from an acceptor, and the first and second group are linked by at least a first linkage, and an increase, of fluorescence of said acceptor due to the decrease, of energy transfer from said acceptor to said quencher resulting from cleavage of said first linkage, is measured.

Characteristic for the invention is that the bioassay comprises iii) a further third group comprising a donor for energy transfer to said acceptor, which donor is an up-conversion fluorescent compound, a long-lifetime fluorescent compound or an electrogenerated luminescent compound; and a conformational or terminal epitope is created on said first group through said cleavage of the linkage, and said third group comprises a binder with affinity for binding to said conformational or terminal epitope; and the fluorescence of said acceptor is brought about by exciting the donor resulting in energy being transferred from the donor to the acceptor.

The present invention also provides a kit that comprises reagents including i) a first group comprising an acceptor, which acceptor is a short lifetime fluorescent compound capable of energy transfer, and ii) a second group linked to said first group by at least a first linkage, said second group comprising a quencher, which quencher is capable of energy transfer from an acceptor, and iii) a third group comprising a donor for energy transfer to said acceptor, which donor is an up-conversion fluorescent compound, a long-lifetime fluorescent compound or an electrogenerated luminescent compound; and said first group being such that a conformational or terminal epitope is created on said first group through cleavage of said first linkage and said third group comprising a binder with affinity for binding to said conformational or terminal epitope.

BRIEF DESCRIPTION OF THE DRAWINGS

FIG. 6 illustrates the use of dual-labelled oligomer substrate in combination with a donor labelled binder, which binder is specific to conformational epitope of substrate created through cleavage, in a cleavage bioassay according to another embodiment of the present invention.

FIG. 9 illustrates the use of dual-labelled peptide substrate in combination with a donor labelled antibody, which antibody is specific to a terminal epitope of peptide present only when peptide is cleaved at a certain position, in a bioassay measuring activity of protease enzyme according to another example of the present invention.

DETAILED DESCRIPTION OF THE INVENTION

Definitions

Figure 1A:
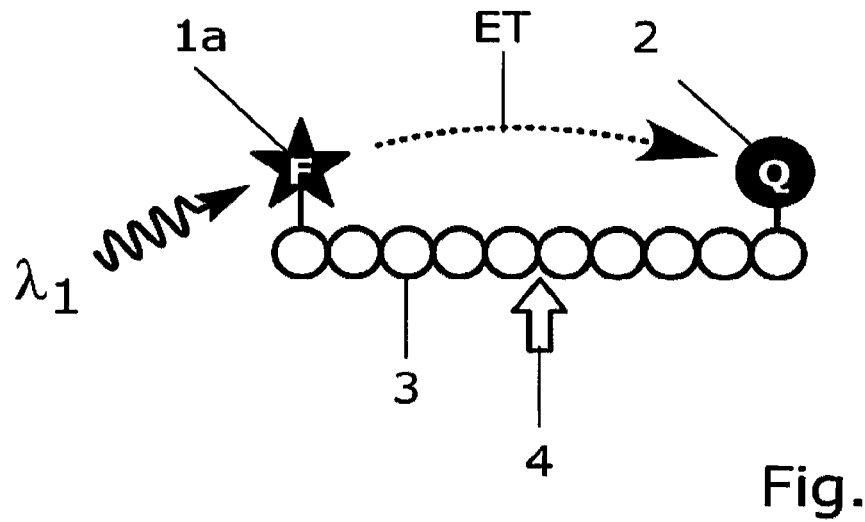
FIG. 1 illustrates the use of dual-labelled oligomer substrate in a prior art cleavage bioassay.

In this disclosure, the term "bioassay" shall be understood to refer to cleavage assays, conformation change assays, and dissociation and association assays. In cleavage assays an intact dual labelled oligomer is cleaved and the distance between two or more parts of the dual labelled oligomer increases; one part of the oligomer contains the fluorescent compound and another quencher compound. In conformation change assays, such as molecular beacon type assays, the conformation of an oligomer is changed due to, for example, binding of modulating compound, increasing the distance between the fluorescent compound and the quencher compound attached to different positions of the oligomer. In dissociation and association assays, for example nucleic acid hybridization assays, the distance between the two labelled oligomers decreases or increases, respectively, upon binding, wherein one oligomer is labelled with a fluorescent compound and another with a quencher compound.

The term "homogeneous bioassay" shall be understood to cover bioassays requiring no separation steps. Single or multiple steps of each; addition of reagents, incubation and measurement are the only steps required. The term "separation step" shall be understood to be a step where a labelled bioassay reagent bound onto a solid-phase, such as for example a microparticle or a microtitration well, is separated and physically isolated from the unbound labelled bioassay reagent; for example the microtitration well is washed (liquid is taken out and, to improve the separation, additional liquid is added and the well emptied) resulting in separation of the solid-phase bound labelled bioassay reagent from the labelled bioassay reagent not bound onto the solid-phase.

The term "fluorescence" shall be understood to cover photoluminescence, i.e. luminescence excited by light, fluorescence, including delayed fluorescence with microsecond or millisecond fluorescence lifetime, ionic photoluminescence, up-conversion based anti-Stokes photoluminescence, and phosphorescence. In addition, the term shall cover electrogenerated luminescence and electrochemiluminescence.

The terms "first group", "second group" and "third group" refer, in the context of the present invention, to reagents of the bioassay. Accordingly these groups are introduced into the assay essentially as defined and are not formed during the assay. Thus, none of the groups can be e.g. formed during the assay by incorporation of an analyte.

The term "fluorescent label" or "fluorescent compound" shall be understood to cover dye molecules, proteins, polymers, particles, dyed particles and phosphors, which express fluorescence.

The terms "acceptor" and "donor" shall be understood to cover fluorescent compounds, which participate in energy transfer processes with another fluorescent compound or a non-luminescent compound.

The terms "non-luminescent" and "non-fluorescent" shall be understood as property of a light absorbing compound not to produce any or a significant amount of luminescence when excited and relaxing from the excited-state. In contrast to luminescent compounds, the excited-state energy of a non-luminescent compound is predominantly relaxed via nonradiative pathways, typically producing heat instead of light. The fluorescence quantum yield of a non-luminescent compound is very poor, typically below 5 percent. Examples of non-luminescent compounds are quencher compounds, which can efficiently participate in energy transfer from a fluorescent compound, but which do not produce any significant luminescence upon excitation.

The term "terminal epitope" shall be understood as an epitope comprising a terminal sequence of a peptide, oligopeptide, oligonucleotide or oligosaccharide, or their synthetic mimics. Characteristics to a "terminal epitope" is that at least a significant part of it is composed by the amino-acid, nucleotide or saccharide in terminal position of the sequence, and that the terminal epitope is not present in a non-terminal sequence.

The term "conformational epitope" shall be understood as an epitope present in a specific secondary or tertiary conformation of a polypeptide, oligopeptide, oligonucleotide or oligosaccharide. In this case, the presence of a "conformational epitope" in the first group is induced by a "cleavage" of a single "linkage" or multiple "linkages" between the first and second group resulting in a change in the conformation of the first group and formation of the "conformational epitope. Characteristics to a "conformational epitope" is that at least a significant part of the epitope is either created or revealed due to change in secondary conformation of a polypeptide, oligopeptide, oligonucleotide or oligosaccharide, and that the "binder" specific to "conformational epitope" has at least five-fold, preferably over ten-fold, increase in affinity towards the first group when the "conformational epitope" is present in the first group.

The term "linkage" shall be understood as a single covalent bond or multiple covalent bonds, such as carbon-carbon bond, or as a single non-covalent bond or multiple non-covalent bonds, such as hydrogen bond, forming either alone or co-operatively a cohesive interaction between the groups linked by the linkage.

The term "cleavage" shall be understood to mean breakage of "linkage" through breakage of a single or multiple covalent bonds, such as carbon-carbon linkage, or non-covalent bond, such as hydrogen bond, resulting in at least partial dissociation of the two groups linked by the "linkage". The cleavage can be a direct or indirect result of enzymatic activity or change of ambient environment, such as a change in pH, ionic strength, concentration, or temperature.

The term "binder" shall be understood as a molecule capable of recognizing and binding to a conformational or terminal epitope. The binder is typically, but not limited to, a protein capable of binding to the conformational or terminal epitope. Examples of such proteins are monoclonal, polyclonal antibodies, recombinant antibodies, scaffold proteins based binders such as engineered repeat proteins, lectins, affibodies, anticalins and trinectins recognizing a terminal peptide, oligonucleotide or oligosaccharide sequence, and PDZ-domain, N-end rule associated binder proteins and 14-3-3-proteins domains recognizing a terminal peptide sequence. The binder can be also an artificial binder such as an aptamer, a metal chelate, an imprinted polymer, a complementary oligonucleotide sequence, or an artificial nucleic acid mimic capable of binding to a conformational or terminal epitope. Preferably the binder has a high affinity to the "terminal epitope" or the "conformational epitope", preferably with an affinity constant over $10^7$ l/mol, more preferably over $10^8$ l/mol and most preferably over $10^9$ l/mol. In addition, the interaction between the binder and the conformation or terminal epitope should be rapid during association and slow during dissociation.

The term "long-lifetime fluorescence" and "long-lifetime fluorescent compound" shall be understood to cover fluorescence and fluorescent compounds having a luminescence lifetime equal to or more than 1 microsecond (the lifetime being calculated as the time wherein luminescence emission intensity decays to the relative value of 1/e, i.e. to approximately 37% of the original luminescence emission intensity). The compounds capable of long-lifetime fluorescence include, but are not limited to, lanthanide chelates, lanthanide-chelate dyed-nanoparticles, lanthanide phosphors and nanophosphors, porphyrins, and porphyrin dyed-nanoparticles.

The term "light" and "excitation light" and "emission light" shall be understood as electromagnetic radiation at wavelengths from 200 nm to 1600 nm. These wavelengths cover ultraviolet, near-ultraviolet, visible, near-infrared and infrared light.

The term "short-lifetime fluorescence" and "short-lifetime fluorescent compound" shall be understood to cover fluorescence and fluorescent compounds with a luminescence lifetime of less than 1 microsecond.

The term "quenched fluorescent substrate" and "quenched fluorescence labelled substrate" shall be understood as a molecule, typically an oligomer, for example an oligopeptide or oligonucleotide, containing both a fluorescent compound and quencher compound capable of energy transfer from a fluorescent compound to quencher compound.

The term "quenched short-lifetime fluorescent substrate" and "quenched long-lifetime fluorescence substrate", respectively, shall be understood as a quenched fluorescent substrate, where the fluorescent compound is a short-lifetime fluorescent compound or a long-lifetime fluorescent compound, respectively.

The terms "quencher", "quencher label" and "quencher compound" shall be understood as non-luminescent or luminescent compound essentially capable of energy transfer from a short-lifetime or long-lifetime fluorescent compound. Typically, but not necessarily, the absorption spectra of the quencher at least partially overlaps with the emission spectra of the donor and the energy transfer from a short-lifetime or long-lifetime fluorescent compound to the quencher compound in proximity can be so effective that the intensity of the fluorescence of the fluorescent compound is decreased over 50%, preferably over 90%, more preferably over 95%, and most preferably over 99%.

The terms "acceptor", "acceptor label" and "acceptor compound" mean luminescent or non-luminescent compounds having typically, but not necessarily, absorption spectra at least partially overlapping with the emission spectra of the donor and essentially capable of energy transfer from the donor.

The terms "donor" and "donor label" shall be understood as fluorescent compounds capable of energy transfer either to an acceptor or quencher compound.

The terms "sensitized emission" and "sensitized acceptor emission" shall be understood as emission of the acceptor label generated by energy transfer from the donor label in proximity upon excitation of the donor label. In case of long-lifetime donor label the sensitized emission has also prolonged fluorescence lifetime. Further, the sensitized emission shall also be understood to cover values of sensitized emission corrected by for example measurement of the donor emission or sample absorbance, or values indicating any ratio of the donor emission and the sensitized emission.

The term "up-conversion fluorescence" and "up-conversion fluorescent compound" means fluorescence produced by and fluorescent compounds converting lower energy incident light to higher energy emitted light. It is also called anti-Stokes fluorescence or anti-Stokes photoluminescence. Anti-stokes photoluminescence material converts low energy light to high energy light. In "up-conversion fluorescence" two or more lower energy photons of the same or different energy are absorbed sequentially, in two or more stages, to generate a single higher energy photon, contrary to simultaneous absorption in two-photon or multi-photon excitation.

The terms "luminescent lanthanide label" and "lanthanide label" shall be understood to include a lanthanide chelate or chelate structure, containing one or more lanthanide ions, an inorganic lanthanide containing phosphor particle, or a polymeric nanoparticle containing either the described lanthanide chelates or the phosphor particles. The lanthanide can represent one single lanthanide element or a combination of several different lanthanide elements.

The term "lanthanide" shall be understood here to be equivalent to "rare earth metal ion" and to include single lanthanide elements and combination of several different lanthanide elements from the following: neodymium, praseodymium, samarium, europium, promethium, gadolinium, terbium, dysprosium, holmium, erbium, thulium, ytterbium and yttrium, especially erbium, praseodymium, thulium, and ytterbium.

The term "up-converting luminescent label" and "up-converting lanthanide label" shall be understood as up-conversion fluorescent compound, i.e. luminescent lanthanide label being able to up-convert a lower energy excitation to a higher-energy emission based on an excitation in two or more stages; meaning that two or more photons are sequentially absorbed to excite the label contrary to simultaneous absorption in two or multi photon excitation. The up-converting lanthanide labels include up-converting lanthanide phosphors and up-converting lanthanide chelates.

The term "up-converting lanthanide chelate" in this context means an up-converting lanthanide label, where a single rare earth ion or a combination of different rare earth ions is chelated to a mono or multinuclear complexing ligand. The ligand may or may not contain a light harvesting structure. The light collection efficiency of individual ions and chelated ligands without a light harvesting structure is poor. Therefore, up-converting rare earth chelates can be designed to contain a ligand with light-harvesting organic or inorganic structures, e.g. another ion, incorporated. The collected energies of two or more photons are transferred one after another by intramolecular nonradiative processes from the singlet to the triplet state of the organic structure, then from the triplet state sequentially to the emissive level of the rare earth ion, which then emits a single photon of characteristic emission.

The term "up-converting lanthanide phosphor" shall be understood as a particulate luminescent lanthanide label capable of up-conversion, wherein a particulate absorbs long wavelength radiation and emits light at shorter wavelength as result of energy pooling of sequential absorption of long wavelength radiation. In certain types of phosphors, a priming dose of energy at shorter wavelength is required to excite and pre-load the phosphor before the up-conversion of long wavelength radiation is possible. The up-converting phosphor can be able to delocalise its excitation from a part or the entire volume of the particulate by internal transfer of energy between similar excited states within the particulate to a single or a few acceptor molecules. This means that a single acceptor can be excited by lanthanides which would otherwise be too far away for energy transfer to be efficient. The diameter of the particulate phosphor is preferable equal or greater than 4 nm and preferably smaller than 10 µm, more preferably smaller than 1 µm.

The term "long-lifetime fluorescent lanthanide label" shall be understood as a long-lifetime fluorescent compound, i.e. a luminescent lanthanide label being able to emit long-lifetime fluorescence upon excitation enabling temporal resolution in fluorescence detection with delay time and gate times equal or greater than 1 microsecond. The long-lifetime lanthanide labels include long-lifetime fluorescent lanthanide phosphors, long-lifetime fluorescent lanthanide-chelate dyed nanoparticles, and long-lifetime fluorescent lanthanide chelates and chelate derivatives. In addition to lanthanide-based compounds the term shall be understood to include platinum and palladium porphyrins and derivatives with similar long-lifetime fluorescence properties.

The term "long-lifetime fluorescent lanthanide chelate" means long-lifetime fluorescent lanthanide label, where a single rare earth ion or a combination of different rare earth ions is chelated to a mono or multinuclear complexing ligand. The ligand may or may not contain a light harvesting structure. The light collection efficiency of individual ions and chelated ligands without light harvesting structure is poor.

The term "long-lifetime fluorescent lanthanide phosphor" and "long-lifetime fluorescent lanthanide-chelate dyed nanoparticle" shall be understood as a particulate luminescent lanthanide label capable of long-lifetime fluorescence. The long-lifetime fluorescent lanthanide phosphor is an inorganic phosphor crystal doped with emissive lanthanide ions. The long-lifetime fluorescent lanthanide-chelate dyed nanoparticle is a polymeric particle dyed with long-lifetime fluorescent lanthanide chelates. The diameter of the particulate phosphor or particle is equal or greater than 4 nm and smaller than 1 µm.

The terms "energy transfer", "fluorescence energy transfer" and "FRET" shall be understood as transfer of excited state energy from donor compound to acceptor or quencher compound in proximity. Typically the energy transfer is based on Förster type fluorescence resonance energy transfer, but especially in case of lanthanide labels other mechanism can be prevalent.

The terms "electrogenerated luminescence" and "electrochemiluminescence" shall be understood as luminescence produced by electrogenerated chemical excitation using an electrode and applying electric current or voltage to electrode. Depending on the electrode where the electrochemical reaction producing luminescence occurs the electrochemiluminescence is called cathodic or anodic electrochemiluminescence. Electrogenerated luminescence compounds are compounds capable of anodic or cathodic electrogenerated luminescence. Examples of such compounds are $Ru(bpy)_3^{2+}$ and its derivatives with red emission and hot electron excited 2,6-bis[N,N-bis(carboxymethyl)-aminomethyl]-4-benzoyl phenol-chelated Tb(III) producing green emission and other lanthanide chelates. Electrogenerated luminescence of lanthanide chelates can also be measured using temporal resolution to improve limit of detection. Further, the electrogenerated luminescence compounds can be embedded in a particulate to amplify the luminescence.

Preferred Embodiments of the Invention

The present invention provides an improved luminescence energy transfer based homogeneous bioassay, suitable for use in measurement of biological activity, its modulation or analyte concentration in a sample. The invention further provides assays which can be carried out by using either long-lifetime luminescent, up-converting luminescent, or electrogenerated luminescent particulate labels as donors to improve signal intensity and limit of detection, which do not need any separation steps and can be measured by fluorometers or other instruments capable of measuring time-resolved fluorescence, up-conversion photo-luminescence, or electrogenerated luminescence, and in case of up-converting luminescent label, which can be performed with a strongly coloured sample.

An improved assay can be achieved by using an arrangement comprising a first group labelled with an energy acceptor and a second group labelled with a quencher. Characteristic to the invention is that an assay comprises also an additional third group labelled with an energy donor, wherein the third group is capable to bind to the first group only through a cleavage resulting in an increase in the distance between the first group and the second group, and wherein the increased distance between the first group and the second group is observed by excitation of the energy donor of the third group and measuring the emission of the acceptor.

Thus, a typical embodiment of this invention concerns a luminescence energy transfer based homogeneous bioassay comprising a first group labelled with an energy acceptor, a second group labelled with a quencher, and a third group labelled with an energy donor, wherein
- the energy acceptor is a short-lifetime fluorescent label, said label being able to fluorescence energy transfer to the quencher,
- the quencher is either a luminescent or a non-luminescent label,
- the energy donor is a long-lifetime luminescent label, a up-conversion luminescent label, or electrogenerated luminescent label, said label being able to fluorescence energy transfer to acceptor,
- the first group and the second group are linked by at least a first linkage,
- the first linkage is cleaved,
- a conformational or terminal epitope is created on said first group through said cleavage of the first linkage,
- the third group comprises a binder with affinity for binding to said conformational or terminal epitope, and
- the decrease in energy transfer from the acceptor to the quencher resulting from lengthening of the distance between said labels resulting from cleavage of said first linkage is observed by exciting the energy donor and measuring the increase in the sensitized emission of the energy acceptor.

According to a typical embodiment of the invention,
- the assay is performed by contacting the first group and the second group, and preferably also the third group, with the sample,
- the assay is incubated for biological activity, for modulation of the biological activity or binding of analyte either to the first or the second group or to both groups,
- the third group is added into the assay, unless added earlier,
- the assay is incubated for binding of the first group to the third group, and
- the energy donor is excited and the sensitized emission of the energy acceptor is measured; the magnitude of said sensitized emission being indicative of the distance between the first group and the second group.

According to one advantageous embodiment, the third group is in the form of particulate, each particulate comprising at least a single said donor and said binder, and preferably comprising multiple of said donors and said binders. One or several, preferable a multitude, of particulates for each assay are used. Preferably the particulate is in the form of microparticle, having a diameter less than 10 micrometers, more preferably in the form of nanoparticle, having diameter less than 400 nanometers, and most preferably in the form of nanoparticle, having diameter less than 100 nanometers and preferably equal to or larger than 4 nm.

The invention provides a unique combination of features to improve homogeneous, non-separation bioassays based on luminescence detection:

1) signal of the assay (sensitized accepter emission) is strictly dependent on the distance between two labels, an acceptor and a quencher, since fluorescence resonance energy transfer is dependent to inverse sixth power of distance,
2) signal of the assay is not significantly generated by acceptor when quencher is in proximity, enabling low background signal independent of donor and acceptor concentrations,
3) signal of the assay can be amplified by using a particulate donor or multiple donors, enabling high signal when acceptor and quencher are not in proximity with each other, yet enabling low background signal when acceptor and quencher are in proximity with each other,
4) signal of the assay can be measured without competition in binding to third group between entities containing both the first group and the second group at short distance and at long distance, as only those entities, wherein the distance between the first group and the second group is increased, are bound; and thus no excess of third group is needed contrary to the invention described in an unpublished patent application PCT/FI2006/000379,
5) signal of the assay can be measured or monitored real-time during the assay, when the third group is added simultaneously with the first group and the second group; the third group is only bound to the first group after the cleavage of the first linkage and thus the binding of the third group does not interfere sterically or by other means the biological activity resulting in the cleavage of the first linkage, which is an improvement over the invention described in an unpublished patent application PCT/FI2006/000379,
6) signal of the assay based long-lifetime fluorescent donor can be measured free of autofluorescence with temporal resolution, and
7) signal of the assay based up-converting fluorescent donor can be measured free of autofluorescence and scattered excitation light without temporal resolution at a wavelength range where most of the biological samples are practically transparent.

Enzymatic activity of proteases, peptidases and nucleases and effect of possible inhibitors and other modulating compounds to enzymatic activity is commonly measured by using quenched fluorescence labelled peptide or oligonucleotide substrate. Both conventional short-lifetime fluorescent compounds and long-lifetime fluorescent compounds have been employed. Monitoring cleavage of effectively quenched long-lifetime fluorescence labelled substrate by measuring the fluorescence of the fluorescence moiety results in increasing signal with increasing amount of cleaved substrate and typically small amounts of cleaved substrate (i.e. small amount of cleaving agent e.g. enzyme present or the cleaving agent is only weakly active) can be distinguished from background signal using temporal resolution, which eliminates autofluorescence, in measurement. The use of a quenched substrate labelled with short life-time fluorescent compounds produces also increasing signal, but a high background fluorescence does not allow the detection of as small amounts of cleaved substrate as with long-lifetime fluorescence labelled substrates.

The synthesis of long-lifetime fluorescence labelled substrates is, however, more difficult and expensive than short-lifetime fluorescence labelled substrates. In addition long-lifetime fluorescence or up-conversion fluorescence originated from a particulate label cannot be effectively quenched and thus the detection of cleavage of a small amount of substrate is difficult to distinguish from the background although the signal is well measurable. The present invention describes how these limitations can be avoided and the detection of the cleavage of the short-lifetime fluorescence labelled substrates can be significantly improved by detecting the fluorescence of a cleaved short-lifetime fluorescence labelled substrate by energy transfer from a long-lifetime fluorescence or up-conversion fluorescence compound.

The present invention has significant advantages over previously described methods employing particulate labels as it results in an increasing signal with increasing amount of cleaved substrate and enables detection of small amount of cleaved substrate. In addition to the measurement of cleavage of a quenched substrate the present invention can be employed in detection of a change of conformation of a double labelled compound, or association and dissociation of a pair of molecules containing a fluorescent compound and a quencher compound in different parts, capable of binding to each other, of the molecule pair. The use of an up-conversion fluorescence compound as a donor enables also measurement in strongly coloured samples as measurement can be performed using both excitation and emission wavelengths in far-red, near-infrared and infrared—above the major absorption of any biological sample.

According to what is known from prior art a particulate donor label is difficult to be quenched by a single binding event due to the large size of the label. The present invention, however, solves this problem, as a large amount of the fluorescence of the particulate donor label can be transferred to a single acceptor label with can be quenched very efficiently. Thus by using three labels of which one is a particulate label as described in the present invention, the particulate label can be efficiently employed in a fluorescence quenching based assay.

According to what is further known from prior art the particulate lanthanide label is not sensitive to environment in contrast to lanthanide chelates and cryptates. The luminescence of intrinsically fluorescent lanthanide chelates is sensitive to low pH, high concentration of metal chelators, and certain metal ions, for example $Mn^{2+}$ $Cr^+$, $Co^{2+}$, $Fe^{2+/3+}$ and $Cu^{2+}$ can efficiently quench the luminescence of lanthanide chelates. Thus according the present invention, the particulate lanthanide label can be employed in assays where lanthanide chelates are not suitable.

According to the invention the use of a particulate donor provides improved performance but a conventional small molecule long-lifetime fluorescent, an up-conversion fluorescent, or an electrochemically excited fluorescent label can also be employed as a donor to provide a significant improvement over prior art.

A typical assay according to the invention is a homogenous bioassay for use in measurement of biological activity, its modulation or analyte concentration of a sample, said bioassay comprising: a first group comprising an acceptor, which acceptor is a short lifetime fluorescent compound capable of energy transfer, a second group comprising a quencher, which quencher is capable of energy transfer from an acceptor, and the increase of fluorescence of said acceptor due to the decrease of energy transfer from said acceptor to said quencher resulting from lengthening of the distance between said acceptor and quencher is measured. The lengthening of said distance results from cleavage of a first linkage between the first group and the second group and a conformational or terminal epitope is created on said first group through said cleavage of the first linkage. The bioassay comprises a further third group comprising a donor for energy transfer to said acceptor, which donor is an up-conversion fluorescent compound, a long-lifetime fluorescent compound or an electrogenerated luminescent compound; said third group comprises a binder with affinity for binding to said conformational or terminal epitope created on said first group. The fluorescence of said acceptor is brought about by exciting the donor resulting in energy being transferred from the donor to the acceptor.

In preferred embodiments of an assay according to the invention the quencher is non-luminescent. In preferred embodiments of the assay according to the invention the donor is excited either by light or electrochemically.

In some embodiments of the invention the first group and the second group are covalently linked by a covalent linkage, and lengthening of the distance between the acceptor and quencher results from cleavage of the first group from the second group by cleavage of the covalent linkage.

In other embodiments of the invention the first group and/or the second group comprises an oligopeptide, oligonucleotide or oligosaccharide. The cleavage of the first group from the second group is preferably enzymatic.

In further embodiments of the invention the first group and the second group are linked by yet another linkage and the length lengthening of the distance between the acceptor and quencher results from the cleavage of the first linkage, which is either non-covalent linkage or covalent linkage. Typically the first group and/or the second group comprises an oligopeptide, oligonucleotide or oligosaccharide.

The typical assay according to the invention comprises the steps of
a) bringing the sample, the first group, the second group and preferably the third group, in contact with each other to obtain an assay mixture,
b) allowing the assay mixture to react,
c) bringing the third group in contact with the assay mixture if it was not brought in contact with the assay mixture in step a),
d) allowing the third group to react with the assay mixture if it was brought in contact with the assay mixture in step c),
e) exciting the donor, and
f) measuring the sensitized emission of the acceptor.

In some embodiments of the invention the third group is brought in contact with the assay mixture in step c) and allowed to react with the assay mixture in step d).

In some preferred embodiments of the invention the third group is a particulate comprising one or more donors and one or more binders. Typically the particulate has a diameter of <10 μm, preferably <400 nm, and more preferably <100 nm.

In other preferred embodiments of the invention the third group is incorporated in a solid-surface or a surface coating comprising one or more donors and one or more binders.

The bioassay according to this invention can be either a non-competitive assay or a competitive assay.

The bioassay according to the present invention is preferred to be carried out in two incubation steps, the second incubation step being the binding reaction of the binder of the third group to the epitope of the first group after addition of the third group.

The invention also concerns kits for homogenous bioassays according to the invention. The quencher is preferably non-luminescent.

In some preferable embodiments of the kit the first group and the second group are covalently linked, by a covalent linkage. The first group and/or the second groups can comprise an oligopeptide, oligonucleotide or oligosaccharide.

In other preferable embodiments the reagents of the kit are tailored according to typical and/or preferred embodiments of the method of the invention as disclosed above.

In many preferred embodiments of the kit the third group is a particulate comprising one or more donors and one or more binders. The particulate typically has a diameter of <10 μm, preferably <400 nm, and more preferably <100 nm.

In other preferred embodiments of the kit the third group is incorporated in a solid-surface or a surface coating comprising one or more donors and one or more binders.

DESCRIPTION OF THE DRAWINGS

Figure 1B:
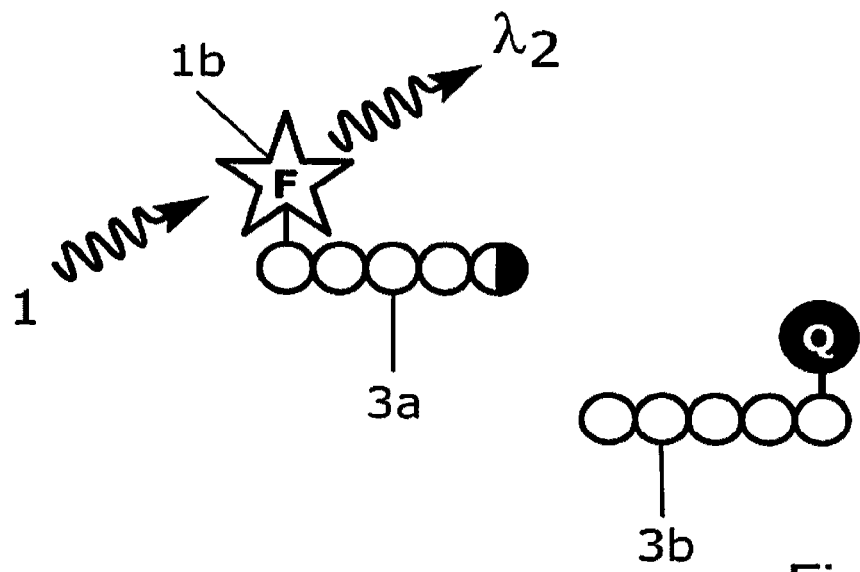

FIGS. 1a and 1b illustrate the use of a dual-labelled 1a, 2 oligomer substrate 3 in a cleavage bioassay known from prior art. FIG. 1a shows an intact oligomer substrate 3 labelled with fluorescent compound 1a and quencher 2. The intact oligomer 3 has at least one cleavage site 4 where the oligomer 3 can be split to two oligomers or oligomer units. FIG. 1b shows the same oligomer substrate cleaved to two oligomers 3a, 3b. The intact dual-labelled oligomer substrate 3 containing fluorescent compound 1a is not fluorescent upon excitation of the fluorescent compound at excitation wavelength $\lambda_1$, because the excited-state energy of the fluorescent compound is transferred to the non-luminescent quencher 2 and relaxed nonradiatively. The part of the cleaved substrate 3a labelled with fluorescent compound 1b is fluorescent at emission wavelength $\lambda_2$. The amount of fluorescence at emission wavelength $\lambda_2$ is dependent on cleavage of the intact oligomer substrate 3. Energy transfer is abbreviated ET.

Figure 2A:
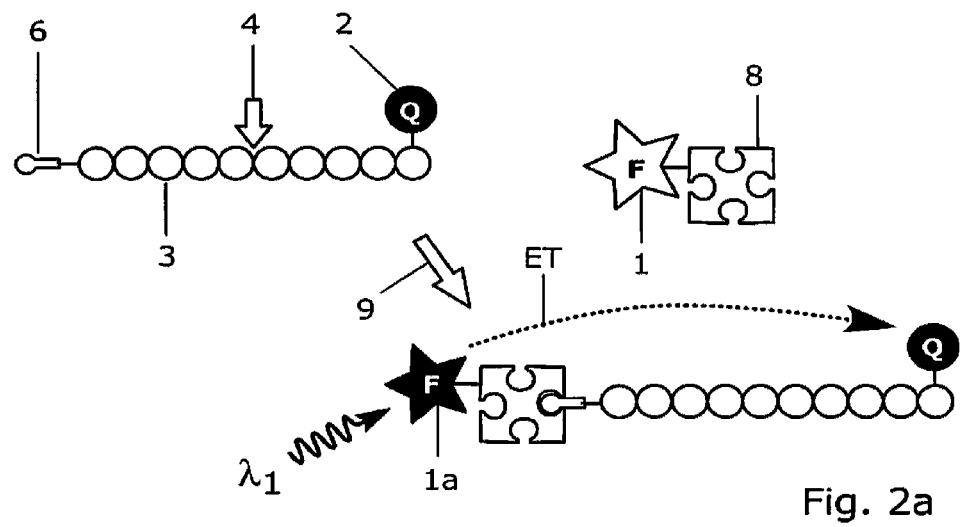
FIG. 2 illustrates the use of quencher labelled tagged oligomer substrate in combination with fluorescent compound labelled binder in another prior art cleavage bioassay.
Figure 2B:
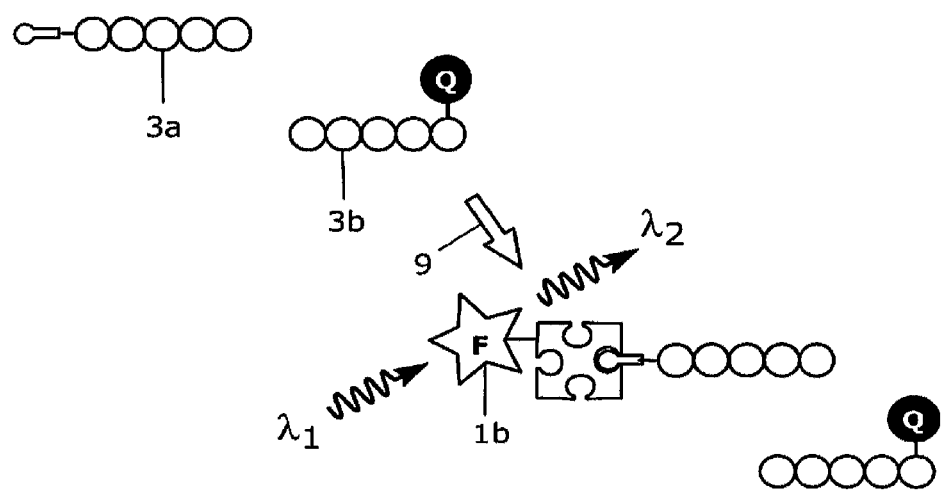

FIGS. 2a and 2b illustrate the use of a quencher 2 labelled tagged 6 oligomer substrate 3 in combination with a fluorescent compound 1 labelled binder 8 in a cleavage bioassay known from prior art. FIG. 2a shows an intact oligomer substrate 3 containing a tag 6 and labelled with a quencher 2. The intact oligomer 3 has at least one cleavage site 4 where the oligomer 3 can be split to two oligomers or oligomer units. A binder 8 labelled with a fluorescent compound 1 can bind 9 to the tag 6 of the oligomer 3. FIG. 2b shows the same substrate cleaved to two oligomers 3a, 3b. FIG. 2a shows how the tag 6 containing quencher 2 labelled intact oligomer substrate 3 quenches the fluorescence of the fluorescent compound 1a and no fluorescence is produced upon excitation of the fluorescent compound 1a at excitation wavelength $\lambda_1$. In FIG. 2b, however, the fluorescent compound 1b of the binder is fluorescent at emission wavelength $\lambda_2$, because the part 3a of the cleaved substrate not containing the quencher 2 is bound and thus the quencher 2 is not in proximity. The amount of fluorescence at emission wavelength $\lambda_2$ is dependent on cleavage of the intact oligomer substrate 3.

Figure 3A:
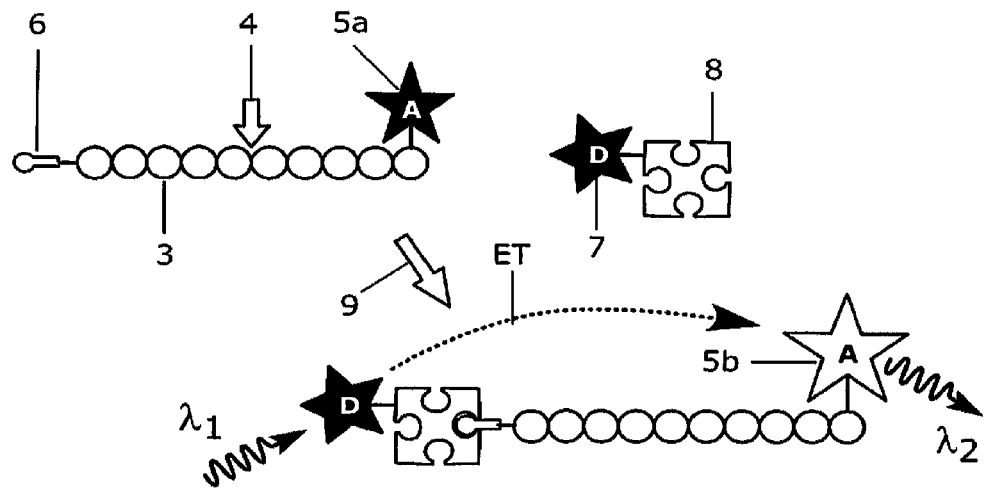
FIG. 3 illustrates the use of acceptor labelled tagged oligomer substrate in combination with donor labelled binder in a further prior art cleavage bioassay.
Figure 3B:
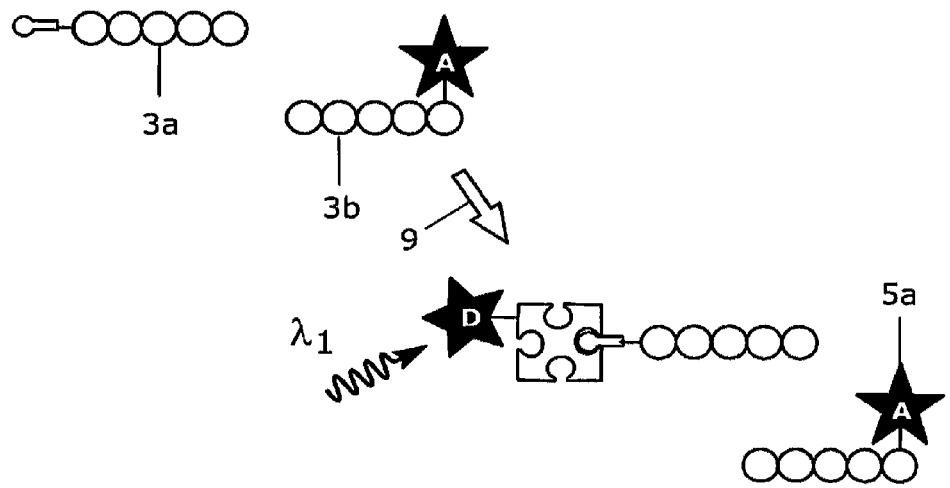

FIGS. 3a and 3b illustrate the use of a acceptor 5a labelled tagged 6 oligomer substrate 3 in combination with a donor 7 labelled binder 8 in a cleavage bioassay known from prior art. FIG. 3a shows an intact oligomer substrate 3 containing a tag 6 and labelled with an acceptor 5a. The intact oligomer 3 has at least one cleavage site 4 where the oligomer 3 can be split to two oligomers or oligomer units. A binder 8 labelled with a donor 7 can bind 9 to the tag 6 of the oligomer 3. FIG. 3b shows the same substrate cleaved to two oligomers 3a, 3b. FIG. 3a shows how the acceptor label 5b of the tag 6 containing acceptor labelled intact oligomer substrate 3 can receive the excited-state energy of the donor 7 and sensitized emission at emission wavelength $\lambda_2$ is produced upon excitation of the donor 7 at excitation wavelength $\lambda_1$. In FIG. 3b, however, the donor 7 of the binder 1b is not in proximity of the acceptor 5a and no sensitized emission is produced at emission wavelength $\lambda_2$, because the part 3a of the cleaved substrate not containing the acceptor is bound. The amount of fluorescence at emission wavelength $\lambda_2$ is inversely dependent on cleavage of the intact oligomer substrate 3.

Figure 4A:
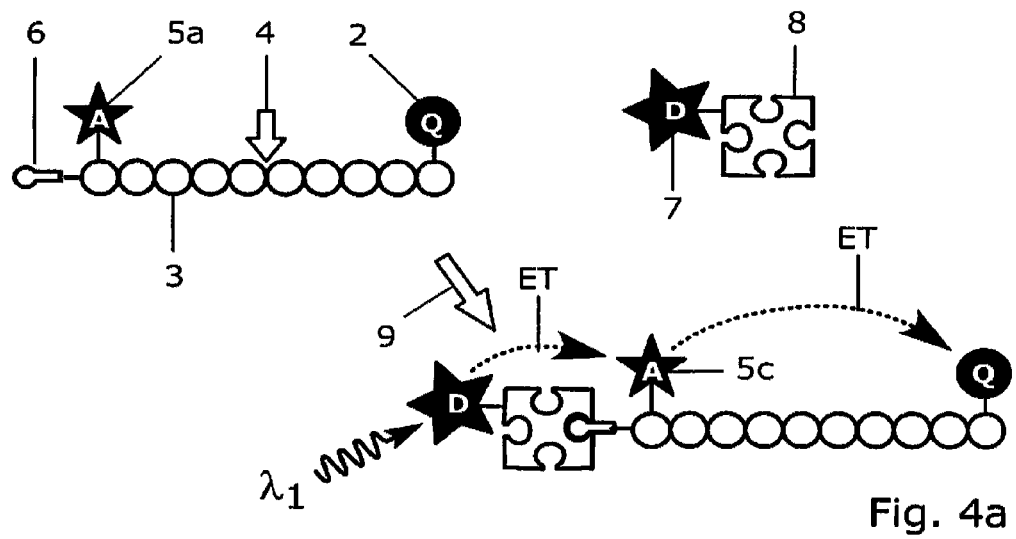
FIG. 4 illustrates the use of dual-labelled tagged oligomer substrate in combination with a donor labelled binder in a cleavage bioassay according to WO 2007/060280.
Figure 4B:
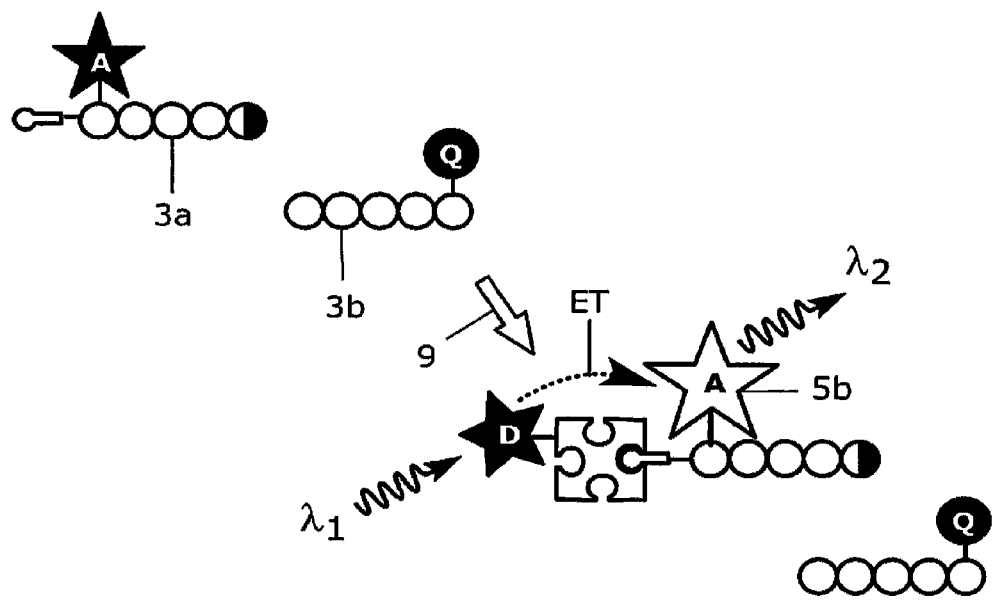

FIGS. 4a and 4b illustrate the use of a dual-labelled 2, 5a tagged 6 oligomer substrate 3 in combination with a donor 7 labelled binder 8 in a cleavage bioassay according to an unpublished patent application PCT/FI2006/000379. FIG. 4a shows an intact oligomer substrate 3 containing a tag 6 and labelled with both an acceptor 5a and a quencher 2. The intact oligomer 3 has at least one cleavage site 4 where the oligomer 3 can be split to two oligomers or oligomer units. A binder 8 labelled with a donor 7 can bind 9 to the tag 6 of the oligomer 3. FIG. 4b shows the same substrate cleaved to two oligomers 3a, 3b; one oligomer 3a containing the tag 6 and the acceptor 5b, the other oligomer 3b the quencher 2. FIG. 4a shows how the intact oligomer substrate 3 containing the tag 6, the acceptor 5c, and the quencher 2 labels can receive the excited state energy of the donor 7, but no sensitized emission at emission wavelength $\lambda_2$ is produced upon excitation of the donor 7 at excitation wavelength $\lambda_1$ due to quenching of the fluorescence. In FIG. 4b, however, the quencher 2 is not in proximity of the acceptor 5b and sensitized emission from the acceptor is produced at emission wavelength $\lambda_2$ upon excitation of the donor, because the part 3a of the cleaved substrate containing the acceptor 5a and the tag 6 but not the quencher 2 is bound to the binder 8 containing the donor 7. The amount of fluorescence at emission wavelength $\lambda_2$ is dependent on cleavage of the intact oligomer substrate 3.

Figure 5A:
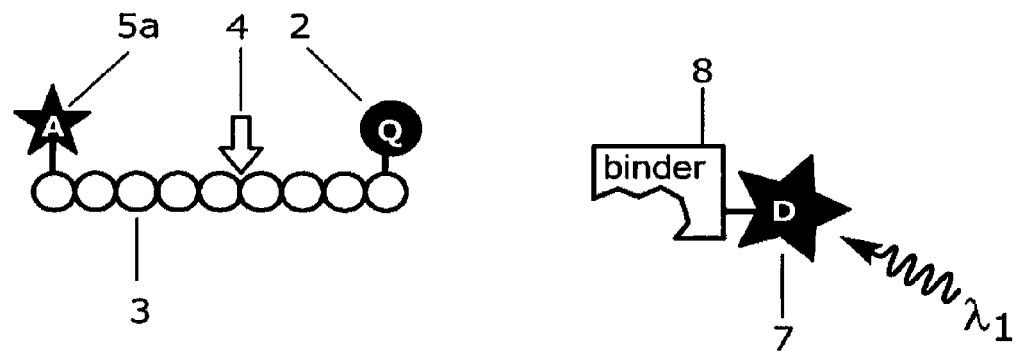
FIG. 5 illustrates the use of dual-labelled oligomer substrate in combination with a donor labelled binder, which binder is specific to terminal epitope of substrate created through cleavage, in a cleavage bioassay according to one embodiment of the present invention.
Figure 5B:
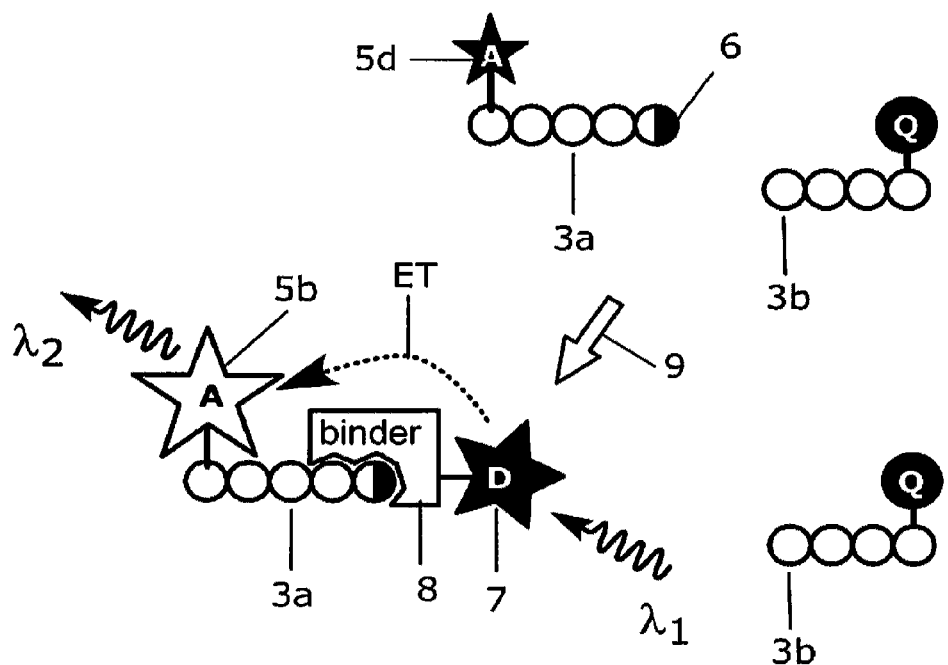

FIGS. 5a and 5b illustrate the use of a dual-labelled 2, 5a oligomer substrate 3 in combination with a donor 7 labelled binder 8 recognizing a terminal epitope in a cleavage bioassay according to one embodiment of the present invention. FIG. 5a shows an intact oligomer substrate 3 labelled with both an acceptor 5a and a quencher 2. The intact oligomer 3 has at least one cleavage site 4 where the oligomer 3 can be split to two oligomers or oligomer units. A binder 8 labelled with a donor 7 cannot bind to the intact oligomer substrate 3 where terminal epitope is not present. FIG. 5b shows the same oligomer substrate cleaved to two oligomers 3a, 3b; one oligomer 3a containing a terminal epitope 6 and the acceptor 5b, the other oligomer 3b containing the quencher 2. FIG. 5a shows that no sensitized emission at emission wavelength $\lambda_2$ is produced upon excitation of the donor 7 at excitation wavelength $\lambda_1$ when the oligomer substrate 3 is intact, because the binder 8 labelled with the donor 7 cannot bind to the intact oligomer substrate 3 and the acceptor 5a is not excited by energy transfer from the donor 7. In FIG. 5b, however, the binder 8 containing the donor 7 can bind 9 to the part of the cleaved oligomer substrate 3a containing both a terminal epitope 6 and the acceptor 5d, and thus sensitized emission from the acceptor 5b is produced at emission wavelength $\lambda_2$ upon excitation of the donor 7. The amount of fluorescence at emission wavelength $\lambda_2$ is dependent on cleavage of the intact oligomer substrate 3.

FIGS. 6a and 6b illustrate the use of a dual-labelled 2, 5a oligomer substrate 3 in combination with a donor 7 labelled binder 8 recognizing a conformational epitope in a cleavage bioassay according to another embodiment of the present invention. FIG. 6a shows an intact oligomer substrate 3 labelled with both an acceptor 5a and a quencher 2. The intact oligomer 3 has at least one cleavage site 4 where the oligomer 3 can be split to two oligomers or oligomer units. A binder 8 labelled with a donor 7 cannot bind to the intact oligomer substrate 3, where conformational epitope is not present. FIG. 6b shows the same oligomer substrate cleaved to two oligomers 3a, 3b; one oligomer 3a containing a conformational epitope 6 and the acceptor 5b, the other oligomer 3b containing the quencher 2. FIG. 6a shows that no sensitized emission at emission wavelength $\lambda_2$ is produced upon excitation of the donor 7 at excitation wavelength $\lambda_1$ when the oligomer substrate 3 is intact, because the binder 8 labelled with the donor 7 cannot bind to the intact oligomer substrate 3 and the acceptor 5a is not excited by energy transfer from the donor 7. In FIG. 6b, however, the binder 8 containing the donor 7 can bind 9 to the part of the cleaved oligomer substrate 3a containing both a conformational epitope 6 and the acceptor 5d, and thus sensitized emission from the acceptor 5b is produced at emission wavelength $\lambda_2$ upon excitation of the donor 7. The amount of fluorescence at emission wavelength $\lambda_2$ is dependent on cleavage of the intact oligomer substrate 3.

Figure 7A:
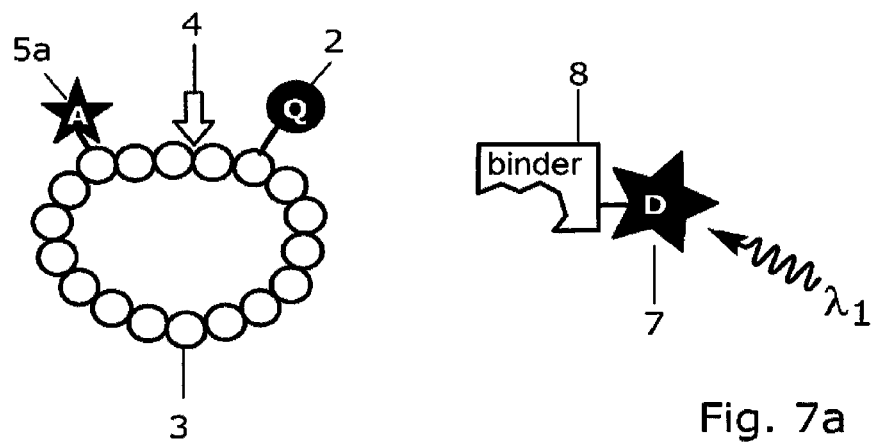
FIG. 7 illustrates the use of dual-labelled cyclic oligomer substrate in combination with a donor labelled binder, which binder is specific to terminal epitope of linearized substrate created through cleavage, in a cleavage bioassay according to yet another embodiment of the present invention.
Figure 7B:
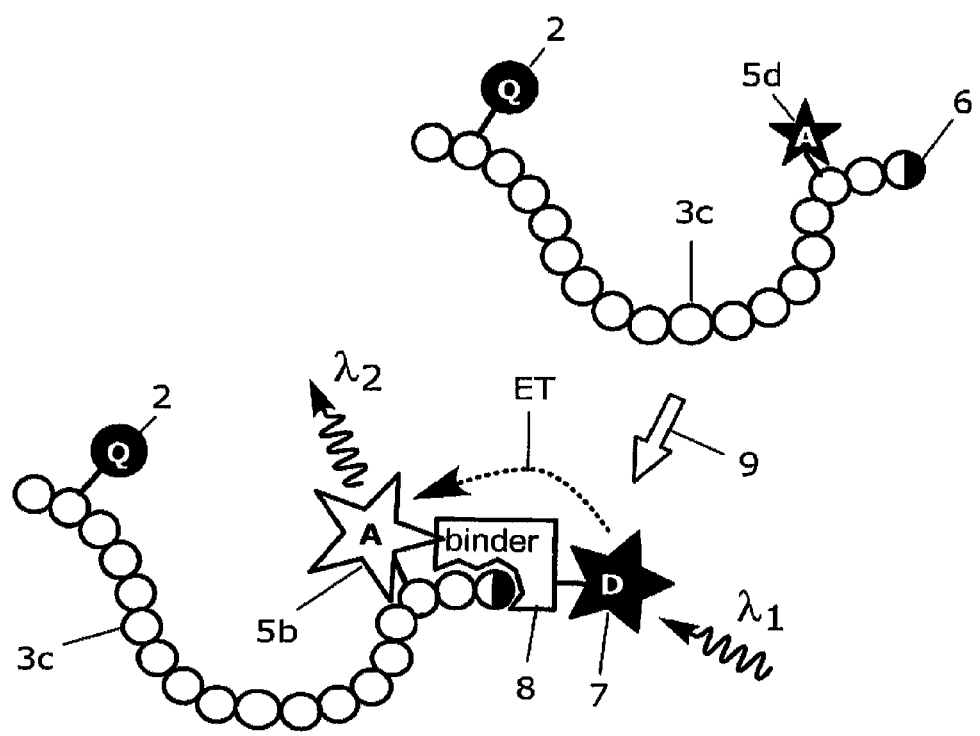

FIGS. 7a and 7b illustrate the use of a dual-labelled 2, 5a circular oligomer substrate 3 in combination with a donor 7 labelled binder 8 recognizing a terminal epitope in a cleavage bioassay according to yet another embodiment of the present invention. FIG. 7a shows a circular oligomer substrate 3 labelled in adjacent positions with both an acceptor 5a and a quencher 2. A binder 8 labelled with a donor 7 cannot bind to the circular oligomer 3, where no terminal epitope is present. The circular oligomer 3 has at least one cleavage site 4 where the circular oligomer 3 can be cleaved to a linearized oligomer 3c as shown in FIG. 7b in a way that the distance between the acceptor 5d and the quencher 2 is increased and a terminal epitope 6 is created into the terminal end of the linearized oligomer 3c adjacent to the acceptor 5d. FIG. 7a shows that no sensitized emission at emission wavelength $\lambda_2$ is produced upon excitation of the donor 7 at excitation wavelength $\lambda_1$ when the oligomer substrate 3 is circular, because the binder 8 labelled with the donor 7 cannot bind to the circular oligomer substrate 3 and the acceptor 5a is not excited by energy transfer from the donor 7. In FIG. 7b, however, the binder 8 containing the donor 7 can bind 9 to the terminal epitope 6 of the linearized oligomer substrate 3c adjacent to the acceptor 5d, and thus sensitized emission from the acceptor 5b is produced at emission wavelength $\lambda_2$ upon excitation of the donor 7. The amount of fluorescence at emission wavelength $\lambda_2$ is dependent on cleavage of the circular oligomer substrate 3.

Figure 8B:
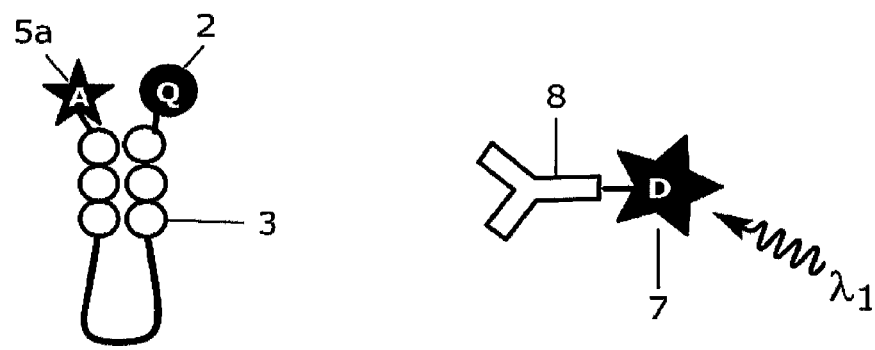
FIG. 8 illustrates the use of dual-labelled calmodulin in combination with a donor labelled antibody, which antibody is specific to a conformational epitope of calmodulin present only when $Ca^{2+}$ is not bound to calmodulin, in a bioassay measuring calcium concentration according to one example of the present invention.
Figure 8B:
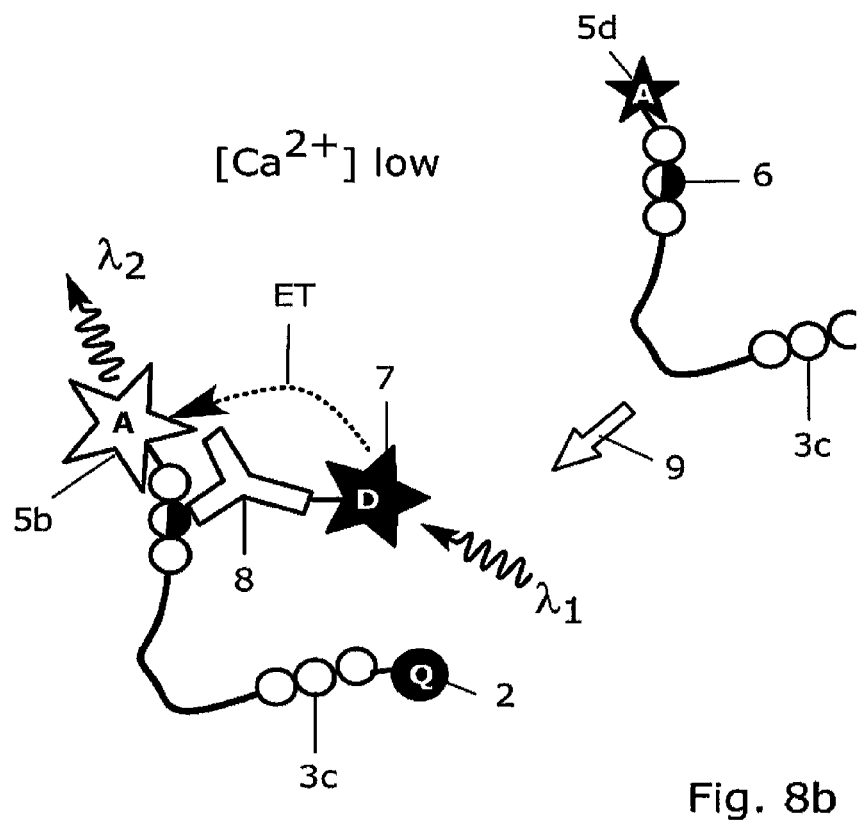

FIGS. 8a and 8b illustrate the use of a dual-labelled 2, 5a calmodulin 3 in combination with a donor 7 labelled antibody 8 specific to $Ca^{2+}$-free conformation of calmodulin in a cleavage bioassay according to Example 3 of the present invention. FIG. 8a shows a calmodulin 3 in $Ca^{2+}$-bound conformation labelled with both an acceptor 5a and a quencher 2. The conformation of calmodulin is responsive to calcium concentration, and at low concentration of calcium, the non-covalent intramolecular bonds are cleaved and calmodulin is converted to $Ca^{2+}$-free conformation 3c creating a conformational epitope 6 adjacent to the acceptor 5d and increasing the distance between the acceptor 5d and the quencher 2 as shown in FIG. 8b. An antibody 8 labelled with a donor 7, shown in FIG. 8a, cannot bind to the $Ca^{2+}$-bound conformation of calmodulin, where the conformational epitope 6 is not present. FIG. 8b shows the calmodulin in $Ca^{2+}$-free conformation 3c containing a conformational epitope 6 adjacent to the acceptor 5b and distant from the quencher 2. FIG. 8a shows that no sensitized emission at emission wavelength $\lambda_2$ is produced upon excitation of the donor 7 at excitation wavelength $\lambda_1$ when the calmodulin 3 is in $Ca^{2+}$-bound conformation, because the antibody 8 labelled with the donor 7 cannot bind to the calmodulin 3 in $Ca^{2+}$-bound conformation 3 and the acceptor 5a is not excited by energy transfer from the donor 7. In FIG. 8b, however, the antibody 8 containing the donor 7 can bind 9 to the conformational epitope 6 of the calmodulin in $Ca^{2+}$-free conformation 3c adjacent to the acceptor 5d, and thus sensitized emission from the acceptor 5b is produced at emission wavelength $\lambda_2$ upon excitation of the donor 7. The amount of fluorescence at emission wavelength $\lambda_2$ is dependent on the calmodulin in Ca2+-free conformation 3c and thus also dependent on calcium concentration.

FIGS. 9a and 9b illustrate the use of a dual-labelled 2, 5a peptide substrate 3 in combination with a donor 7 labelled antibody 8 recognizing a terminal epitope in a cleavage bioassay according to Examples 1 and 2 of the present invention. FIG. 9a shows an intact peptide substrate 3 labelled with both an acceptor 5a and a quencher 2. The peptide substrate 3 has a cleavage site 4 where the peptide 3 can be split to two peptides. An antibody 8 labelled with a donor 7 cannot bind to the intact oligomer substrate 3 where a terminal epitope is not present. FIG. 9b shows the same peptide substrate cleaved to two peptides 3a, 3b; one peptide 3a containing a terminal epitope 6 and the acceptor 5b, the other peptide 3b containing the quencher 2. FIG. 5a shows that no sensitized emission at emission wavelength $\lambda_2$ is produced upon excitation of the donor 7 at excitation wavelength $\lambda_1$ when the peptide substrate 3 is intact, because the antibody 8 labelled with the donor 7 cannot bind to the intact peptide substrate 3 and the acceptor 5a is not excited by energy transfer from the donor 7. In FIG. 9b, however, the antibody 8 containing the donor 7 can bind 9 to the part of the cleaved peptide substrate 3a containing both a terminal epitope 6 and the acceptor 5d, and thus sensitized emission from the acceptor 5b is produced at emission wavelength $\lambda_2$ upon excitation of the donor 7. The amount of fluorescence at emission wavelength $\lambda_2$ is dependent on cleavage of the intact oligomer substrate 3 and thus dependent on the protease activity.

Preferred Donor Labels

Preferred luminescent donor labels of some embodiments of the invention are selected from the group consisting of long-lifetime luminescence labels (fluorescence lifetime over 1 µs), up-converting luminescence labels (excitation at longer wavelength than emission) and electrogenerated luminescence labels (excited by electric voltage or current).

Employment of a long-lifetime particulate donor with a short lifetime fluorescent acceptor in ligand binding assays is described in WO 02/44725 and in WO 2004/096944, containing description of preferred particulate long-lifetime fluorescent donor labels. Time-resolved homogeneous fluorometric assays and a list of preferred small molecule lanthanide labels comprising both cryptates and chelates have been described in U.S. Pat. No. 5,998,146, Mathis G, Probing molecular interactions with homogeneous techniques based on rare earth cryptates and fluorescence energy transfer, *Clin Chem.* 1995; 41: 1391-1397 and WO 98/015830. Preferred long-lifetime fluorescent porphyrin labels have been described in O'Riordan T. C., Ponomarev G. V. Yashunsky D. V., Papkovsky D. B. Homogeneous assays for cellular proteases employing the platinum(II)-coproporphyrin label and time-resolved phosphorescence, Analytical Biochemistry 2005; 342: 111-119 and Burke M., O'Sullivan P., Soini A., Berney H., Papkovsky D. B. Evaluation of the phosphorescent palladium(II)-coproporphyrin labels in separation-free hybridisation assays, *Anal Biochem* 2003; 320, 273-280.

Preferred up-converting lanthanide labels and their applications have been described in Corstjens P et al., *Clin Chem* 2001; 47:1885-1893; Niedbala R S et al., *Anal Biochem* 2001; 293:22-30; van De Rijke F et al., Nat Biotechnol 2001; 19:273-276; and Zijlmans HJMAA et al., *Anal Biochem* 1999; 267:30-36, and in addition in WO 94/07142, U.S. Pat. Nos. 5,674,698, 6,159,686 and 6,312,914. WO 02/44725 also covers the use of long-lifetime fluorescent anti-Stokes phosphors as donors in combination with short-lifetime fluorescent acceptor. The homogeneous assay principle based on up-converting phosphors has been described in WO 98/43072 and in more detail in US 2002/0119485 and Kuningas K et al. Homogeneous Assay Technology Based on Upconverting Phosphors *Anal. Chem.* 2005; 77: 7348-7355. WO 2004/086049 describes the use of anti-Stokes phosphors in homogeneous fluorescence resonance energy transfer assays in whole blood. Up-converting chelates have been described in U.S. Pat. No. 5,891,656 and Faris G W and Hryndza M, *Proc SPIE—Int Soc Opt Eng* 2002; 4626: 449-452. Excitation of up-converting labels can be performed with e.g. pulsed halogen lamps or semiconductor light-emitting diodes or lasers, which are compact, have high power and are also inexpensive (Johnson B D, *Photonics Spectra* 2001; 35: 52). The exciting radiation employed in the up-conversion is not sufficiently energetic to excite background from the sample or surroundings with multi-photon excitation at a wavelength, which would interfere with the measurement.

Preferred electrogenerated luminescence and electrochemiluminescence donor labels have been described by Kulmala S, and Suomi J. Current status of modern analytical luminescence methods *Analytica Chimica Acta,* 2003; 500: 21-69 and Kulmala S., Ala-Kleme T., Latva M., Loikas K., and Takalo H. Hot Electron-Induced Electrogenerated Chemiluminescence of Rare Earth(III) Chelates at Oxide-Covered Aluminum Electrodes. *J. Fluor.* 1998; 8: 59-65. Hot electron-induced excitation of lanthanide chelates, such as phenolic terbium chelates, enables long-lifetime luminescence and improved limit of detection.

The preferred donor compounds can also be embedded in a solid-surface or a surface coating. Biomolecules can be attached to the solid-surface or to the surface coating. Example of a surface coating containing organo-metallic complexes which can participate in energy transfer has been described in US 2002/0076830.

Preferred Acceptor and Quencher Labels

A luminescent acceptor label is preferably excited by absorption of light at the wavelength of major or significant emission of a donor label, and it preferably emits at a wavelength of none or minimal emission intensity of a donor label. Criteria for selection are described e.g. in WO 98/15830 and U.S. Pat. No. 5,998,146. Overlapping of the donor emission spectra and the excitation spectra of the acceptor is not an unconditional requirement. Especially, when luminescent lanthanides are employed as donors the fluorescence resonance energy transfer does not necessarily follow Förster definitions (Laitala V, Hemmila I. Homogeneous assay based on anti-stokes' shift time-resolved fluorescence resonance energy-transfer measurement. *Anal Chem* 2005; 77: 1483-1487; and US 2005/0123957).

Energy from a donor label can be transferred to one or more acceptor labels of the same or different types of acceptor labels. A luminescent acceptor label can be a single luminescent molecule or combination of different luminescent molecules selected to allow increased Stokes' shift as described in patent U.S. Pat. No. 6,673,943. The preferred luminescent acceptor label is selected from the group consisting of rapidly decaying, short-lifetime fluorophores (fluorescence lifetime below 1 µs). The luminescent acceptor label or a part of it can also be a near-infrared fluorescent protein (Trinquet E et al. *Anal Biochem* 2001; 296:232-244; Kronick M N, *J Immunol Methods* 1986; 92:1-13; Fradkov A F, et al., *FEBS Lett* 2000; 479:127-130).

Especially suitable acceptor fluorophores are e.g. fluorescent phycobiliproteins available from Cyanotech Corporation (www.phycobiliprotein.com), Alexa Fluor and BODIPY series available from Molecular Probes (www.probes.com), Cy-dyes from Amersham Biosciences (www.amershambiosciences.com), EVOblue and DY-dyes from Dyomics (ww.dyomics.com), Atto-Dyes from Atto-tec (www.atto-tec.de) and Oyster-dyes from Denovo Biolabels (www.biolabel.de). Dimeric fluorescent energy transfer dyes, tandem dyes and energy-transfer cassettes, comprising two fluorescent molecules are preferred for their property of large and tunable Stokes' shift (U.S. Pat. No. 5,565,554; WO9939203; EP 0747700 A2; Burghart, A et al., *Chem Commun* 2000; 22: 2203-2204) enable utilization of optimal excitation and emission wavelengths.

Selection of acceptors for up-converting lanthanide donor is described in WO 2004/086049 and for long-lifetime lanthanide donor in U.S. Pat. No. 5,998,146 and WO 98/015830. The preferable acceptor label should be selected to have an excitation spectrum with overlaps at least partially with peaks of the emission spectrum of the donor label and has an emission maximum at wavelength where the emission of the donor is at minimal level.

As specific examples can be mentioned allophycocyanin, Cy 3, Alexa 547, Alexa 555, Cy 5, Cy 5.5, Alexa 647 and Alexa 680, which are suitable to be used as acceptor labels together with described long-lifetime lanthanide donor labels, and B-phycoerythrin, R-phycoerythrin, Alexa 546, Alexa 555, Alexa 660, Alexa 680 and Alexa 700, which are suitable to be used as acceptor labels together with described up-converting lanthanide labels as donor labels.

A non-luminescent quencher label can be a single molecule (U.S. Pat. No. 6,329,205B1), gold cluster (Dubertret B, Calame M, and Libchaber A J, *Nat. Biotechnol.* 2001; 19: 365-70) or nanoparticle dyed with light absorbing molecules. Selection of quencher labels is explained in U.S. Pat. No. 5,998,146 and US 2005/0123957. Especially suitable acceptor fluorophores are e.g. DABCYL and QSY-series from Molecular Probes (www.probes.com), Dark Cy-dyes from Amersham Biosciences (www.amershambiosciences.com), Eclipse ™ Dark Quencher -dyes from Epoch Biosciences (www.epochbio.com), Black Hole Quencher dyes from Biosearch Technologies (www.biosearchtech.com), DYQ-dyes from Dyomics (www.dyomics.com), Black Berry Quenchers from Berry&Associates (www.berryassoc.com), and Elle-Quencher from Oswel (www.oswel.com). As specific examples can be mentioned QSY-21 and Black Hole Quencher 3, which are suitable to be used as quencher labels together with described preferred acceptor labels and up-converting or long-lifetime lanthanide donors. Both quencher dyes have strong absorption at 600-700 nm and have no luminescence emission.

Preferred Binders Recognizing Terminal or Conformational Epitopes

The binder molecule(s) conjugated to the fluorescent donor compound or fluorescent donor particle can specifically recognize an epitope on the first group formed, created or revealed as a result of the cleavage of the said first linkage. The binder molecule can distinguish between the first group wherein the cleavage of said first linkage has not occurred and the first group wherein the cleavage has occurred. The binder has preferably over 5-fold higher, and more preferably over 10-fold, and most preferably over 50-fold higher affinity to the first group wherein the cleavage of the said first linkage has occurred as compared to the first group wherein the cleavage of the said first linkage has not occurred. The binder molecule conjugated to the fluorescent donor compound or fluorescent donor particle should have high affinity towards its epitope created, formed or revealed as a result of the cleavage of said first linkage; the affinity constant ($K_a$) of the binder-epitope interaction should preferably be $\geq 1 \times 10^7 \, M^{-1}$ and more preferably $\geq 1 \times 10^8 \, M^{-1}$ and most preferably $\geq 1 \times 10^9 \, M^{-1}$. In the case the epitope is a part of a peptide or polypeptide molecule preferred binders include monoclonal and polyclonal antibodies, recombinant antibodies, aptamers as well as scaffold proteins based binders such as engineered repeat proteins, affibodies, anticalins and trinectins. In case the epitope is an amino or carboxy terminal segment of a peptide or polypeptide, the following natural binders and their engineered variants with improved affinity can be used as binders in addition to the monoclonal, polyclonal antibodies and recombinant antibodies, aptamers as well as scaffold proteins based binders: PDZ-domain, N-end rule associated binder proteins and 14-3-3-proteins.

In the case the substrate molecule, where the epitope for the binder is created, formed or revealed as a result of the cleavage of said first linkage, is a carbohydrate, the binders used can either be artificially raised binder molecules including monoclonal, polyclonal antibodies, recombinant antibody, anticalin, aptamer or based on natural binding proteins such as lectins or their engineered variants.

If the substrate molecule, where the epitope for the binder is created, formed or revealed as a result of the cleavage of said first linkage is a nucleic acid, the preferred binder molecules include single stranded DNA and single stranded RNA and their chemically modified derivatives as well as monoclonal, polyclonal and recombinant antibodies, aptamers and various scaffold protein based binders.

EXAMPLES

Example 1

Antibody 11H3 (0197-100/bA4N-11H3, NanoTools Antikorpertechnik, Germany; indicated with label 8 in FIGS. 9a and 9b) that specifically recognizes the free N-terminal end of the amyloid peptide βA4 (indicated with label 6 in FIG. 9b) is conjugated to Europium(III)-chelate dyed Fluoromax nanoparticles (indicated with label 7 in FIGS. 9a and 9b) 92 nm in diameter, that is obtained from Seradyn Inc (Indianapolis, Ind.). The conjugation is done as described by Suokka, et al. *Anal Chem* 2001; 73:2254-60. Nanoparticles are prewashed with 10 mmol/l phosphate buffer, pH 7.0, on a Nanosep microporous centrifugal filter (300 kDa cut off; Pall Filtron, Northborough, Mass.). Phosphate buffer is added to the particles, and the solution is sonicated with a tip sonicator (Labsonic U; B. Braun, Leverkusen, Germany) at 80 W for 5 s. Carboxyl groups on the surface of nanoparticles are activated with 10 mmol/l N-(3-dimethylaminopropyl)-N9-ethylcarbodiimide and N-hydroxysulfosuccinimide (Fluka, Buchs, Switzerland) for 30 min. The activated particles are washed once with 10 mmol/l carbonate buffer, pH 9.0, and 5 µmol/l antibody 11H3 is added. After 2 h of incubation, the antibody-coated particles are washed five times with a 2 mmol/l Tris-HCl solution, pH 7.0, and stored at 4° C.

Peptide (NH2-Cys-Glu-Val-Asn-Leu-Asp-Ala-Glu-Phe-Arg-His-Asp-Ser-Gly-Lys-COOH) derived from so called "Swedish mutant" of amyloid precursor protein is labelled at the thiol group of its amino terminal cysteine residue as well as at the primary amino group of its carboxy terminal lysine to obtain the following dual labelled peptide (indicated with label 3 in FIG. 9a):

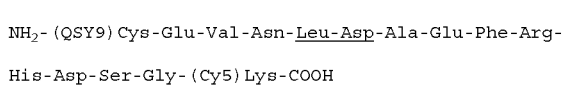

Wherein

QSY9=QSY 9 dye from Invitrogen-Molecular probes, Carlsbad, Calif.

Cy5=CyDye Fluor Cy5 from (GE Healthcare, Finland)

The peptide labelled with Cy5 dye (indicated with label 5a in FIGS. 9a and 9b) at side chain of its carboxy terminal lysine is purchased from Eurogentec, Southampton, UK. The Cy5 labelled peptide is then labelled with QSY9 C5 maleimide reagent (Q30457; Invitrogen-Molecular probes; indicated with label 2 in FIG. 9a) at the thiol group of the amino terminal cysteine according to the instructions by Invitrogen-Molecular probes. The peptide is dissolved in degassed 50 mM phosphate buffer, pH 7.0, in concentration of 100 µM. To guarantee that the thiol group is in reduced form, 1 mM Tris(2-carboxyethyl)phosphine hydrochloride (TCEP, T2556; Invitrogen-Molecular probes) is added, followed by a 10 min incubation under argon gas flow. The QSY9 C5 maleimide reagent is dissolved in dimethylsulfoxide (DMSO) to get a 10 mmol/l stock solution, and this stock solution is added dropwise to the peptide solution to obtain a final concentration of 2 mmol/l QSY9 C5 maleimide reagent. The reaction is incubated for 2 h at room temperature under argon flow, followed by addition of 5 mmol/l β-mercaptoethanol to block unreacted thiol groups of cysteine. The excess of labelling reagent is removed by gel filtration with Sephadex G-25 NAP-5 and NAP-10 columns (GE Healthcare, Finland)

An assay according to the present invention for the detection of cleavage of the dual-labelled target peptide by β-secretase enzyme BASE-1 is set up (FIGS. 9a and 9b). BASE-1 specifically cleaves Swedish mutant of the amyloid precursor peptide by breaking the peptide bond between a Leu and an Asp in the position that corresponds to the residues Leu5 and Asp6 in our dual-labelled model peptide (indicated with label 4 in FIG. 9a; the residues Leu5 and Asp6 are underlined in the sequence of the peptide above). The cleavage of the dual labelled peptide results in two peptides (indicated with labels 3a and 3b in FIG. 9b) of which the one with a new amino terminus (indicated with label 3a in FIG. 9b) contains Cy5 dye attached to the carboxy terminal lysine and the amino terminal sequence of the β4A amyloid peptide that serves as a terminal epitope (indicated with number 6 in FIG. 9b) for the antibody 11H3. The dual labelled peptide is diluted to concentrations of 0.01-10 nmol/l in 100 mmol/l NaAc, pH 4.0 containing 150 mmol/l NaCl. Thereafter, a 20 µl aliquot of each substrate dilution and blank are added into the wells of Fluoro-Nunc 96-well microtiter plates (Nunc, Roskilde, Denmark). 0.2 µg of the human protease BASE-1 (931-AS-050; R&D systems, Minneapolis, Minn.) is added in a 5 µl volume to each well. For each reaction with different substrate peptide concentration, a control reaction with corresponding concentration of substrate peptide but no protease is prepared. The reactions are incubated for 1 h at 37° C. with slow shaking. Then, $5 \times 10^7$ antibody 11H3 conjugated europium chelate-dyed nanoparticles are added to each well in a 25 µl volume of assay buffer (50 mmol/l Tris-HCl, pH 7.75 containing 0.9% (w/v) NaCl, 0.05% (w/v) $NaN_3$, 0.01% (v/v) Tween 40, 0.05% (w/v) bovine-γ-globulin, 20 µmol/l diethylenetriamine-pentaacetate (DTPA) and 0.5% (w/v) BSA). The reactions are incubated for additional 30 min at room temperature with shaking to allow peptides corresponding to the amino terminus of the amyloid peptide 14A to bind to antibody-coated nanoparticles and Cy5 fluorescence is measured thereafter in time-resolved mode by Wallac Victor multilabel counter with an excitation filter at 340 nm, an emission filter at 665 nm, 1000 cycles, delay 75 µs and a window 400 µs.

Example 2

The anti-amyloid peptide 134A antibody 11H3 (indicated with label 8 in FIGS. 9a and 9b) is labelled with fluorescent europium chelate labelling reagent {2,2',2", 2"'-{[2-(4-isothiocyanatophenyl)ethylimino]bis(methylene)bis{4-{[4-(α-ga-lactopyranoxy)phenyl]ethynyl}pyridine-6,2-diyl}bis (methylenenitrilo)}tetrakis(ace-tato)}europium(III) (von Lode P et al., *Anal Chem* 2003; 75: 3193-201; indicated with label 7 in FIGS. 9a and 9b). The labelling of antibody 11H3 is performed in 50 mmol/l sodium carbonate buffer, pH 9.8, using 50-fold molar excesses of the chelate labelling reagent. The reaction is carried out overnight at room temperature and the excess free labelling reagent is removed on NAP-5 and NAP-10 (Amersham Biosciences) chromatography columns using Tris-saline-azide (6.1 g/l Tris, 9.0 g/l NaCl, and 0.5 g/l $NaN_3$), pH 7.75, as elution buffer. The fractions containing the antibody are collected and the europium concentrations are measured against a europium calibrator using DELFIA method (Wallac Oy; Perkinelmer Life and Analytical Sciences, Turku, Finland). Finally, bovine serum albumin is added to a concentration of 1 g/l to the solution containing the europium-labelled antibody. The labelled antibody was stored at 4° C.

Otherwise, the experiment is carried out equally to experiment 1 until 0.5 µmol of fluorescent europium chelate-labelled antibody 11H3 is added to each well in a 25 µl volume of assay buffer instead of addition of $5.10^7$ antibody 11H3-coated europium chelate-dyed nanoparticles. The final concentration of the fluorescent europium chelate-labelled antibody is 10 nmol/l. The reactions are incubated for additional 30 min at room temperature with shaking to allow the labelled antibody to bind to its epitope in the free amino terminus (indicated with label 6 in FIG. 9b) of the amino terminal segment of the amyloid peptide β4A (indicated with number 3a in FIG. 9b), and the Cy5 fluorescence is measured thereafter in time-resolved mode by Wallac Victor multilabel counter with excitation filter at 340 nm, emission filter at 665 nm, 1000 cycles, delay 75 µs and window 400 µs.

Example 3

An assay according to the present invention for the detection of calcium binding related conformational changes in calmodulin was developed (FIGS. 8a and 8b). For the assay, a dual-labelled human calmodulin (indicated with labels 3 and 3c in FIG. 8a) is produced by labelling the amino terminal and carboxy terminal domains of calmodulin with QSY35 dye acting as a quencher compound (indicated with label 2 in FIGS. 8a and 8b) and with Cy5 dye acting as an acceptor group (indicated with label 5a in FIGS. 8a and 8b), respectively. The labelling strategy is adapted from Lang et al., Anal. Biochem. 2005, 342: 271-279, and involves targeting of the first dye to free thiol group of a cysteine engineered to the surface of the protein and the other dye to an engineered selenomethionine residue. For labelling, engineered calmodulin containing mutations threonine 34 to methionine and threonine 110 to cysteine is constructed by site-directed mutagenesis as described by Lang et al., (Anal. Biochem. 2005, 342: 271-279). To introduce a selenomethionine residue (Se-Met) in the position 34 mutated to methionine, the mutated calmodulin is overexpressed in *E. coli* cells in a medium enriched with L-selenomethionine and purified as described by Lang et al., (Anal. Biochem. 2005, 342: 271-279). The buffer of the purified protein is changed to 50 mM buffer, pH 7.0 containing 150 mmol/L NaCl by gel filtration on PD-10 column (Amersham Biosciences). The residue Cys10 in the engineered calmodulin is first targeted with Cy5 maleimide reagent (PA23031; GE Healthcare, Finland) according to the instruction of the labelling reagent provider. The engineered calmodulin is diluted to concentration 1.0 mg/ml in 500 µl of phosphate 50 mM buffer, pH 7.0, containing 150 mmol/L NaCl, and the solution is degassed under vacuum. To reduce the thiol group of the residue Cys10 in the engineered calmodulin, 1 mM Tris(2-carboxyethyl)phosphine hydrochloride (TCEP, T2556; Invitrogen-Molecular probes) is added followed by a 10 min incubation under argon gas flow. The Cy5 maleimide reagent is dissolved in DMSO to give a 40 mmol/l stock solution, and the stock solution is added drop by drop to the protein solution to obtain a final concentration of 4 mmol/l Cy5 maleimide reagent. The reaction is incubated for 4 h at room temperature under argon flow followed by addition of 10 mmol/l β-mercaptoethanol to block unreacted thiol groups. The excess of labelling reagent and β-mercaptoethanol are removed by gel filtration with Sephadex G-25 NAP-10 and PD-10 columns (GE Healthcare, Finland). To introduce the second label to the calmodulin, the Cy5 labelled calmodulin is labelled with QSY 35 iodoacetamide (Q20348; Invitrogen-Molecular probes) targeting Se-Met34 using a protocol modified from Lang et al., (Anal. Biochem. 2005, 342: 271-279). First, the Cy5 labelled calmodulin (in 50 mmol/l phosphate buffer pH 7.0 containing 150 mmol/l NaCl) is concentrated to concentration 1 mg/ml by ultrafiltration (Amicon Ultra-4, kDa, Millipore, Finland). QSY35 iodoacetamide is dissolved in DMSO to give a 50 mmol/l stock solution. QSY35 iodoacetamide stock solution is added to the protein solution dropwise to give final concentration of 5 mM for the labelling reagent. The reaction is incubated for 4 h at room temperature, and, thereafter, the excess of the labelling reagent is removed by gel filtration with NAP-10 and PD-10 columns using 50 mmol/l phosphate buffer, pH 7.0 containing 150 mmol/l NaCl as an eluent.

Conformation specific anti-calmodulin rabbit antisera (indicated with label 8 in FIGS. 8a and 8b) is produced against peptide derived from residues 141-148 of bovine calmodulin as described by Gariépy et al., 1986, Proc. Natl. Acad. Sci. USA 83, 8888-8892. The antisera described by Gariépy et al., 1986, Proc. Natl. Acad. Sci. USA 83, 8888-8892) binds to the calmodulin only in the absence of $Ca^{2+}$ or in the presence of very low concentration of it (<<1 mM). The antisera is purified with 5 ml protein G Sepharose Fast Flow affinity chromatography (GE Healthcare, Finland) according the protocol by the column manufacturer. In brief, the column is equilibrated with 5 column volumes of binding buffer (20 mmol/l sodium phosphate, pH 7.0). The antisera is applied to the column and the column is washed with 10 volumes of the binding buffer. The bound immunoglobulin is eluted with 0.1 mol/l glycine-HCl, pH 2.7 and 1 ml fractions are collected. The pH of the eluent is neutralized immediately after elution by adding 150 μl of 1 mol/l Tris-HCl, pH 9.0 to each fraction. The purified anti-calmodulin immunoglobulin is conjugated to Europium(III)-chelate dyed Fluoromax nanoparticles (indicated with label 7 in FIGS. 8*a* and 8*b*) 92 nm in diameter as described in the Example 1 for antibody 11H3. The dual-labelled calmodulin in calcium bound conformation (indicated with label 3 in FIG. 8*a*) is diluted to concentrations of 0.01-10 nmol/l in 100 mmol/l Na-phosphate, pH 7.0 containing 1 mmol/l $CaCl_2$ and 150 mmol/l NaCl. Thereafter, a 20 μl aliquot of each substrate dilution and blank is added into the wells of Fluoro-Nunc 96-well microtiter plates (Nunc, Denmark). To induce the conformational change due to the removal of $Ca^{2+}$ from calmodulin, metal chelating agent ethylene glycol tetraacetic acid (EGTA) is added in various concentrations (0, 100 μM, 1 mM and 5 mM) to the reactions in a volume of 5 μl. The reactions are incubated for 30 min at 37° C. with slow shaking. Then, $5\times10^7$ anti-calmodulin immunoglobulin conjugated europium chelate-dyed nanoparticles are added to each well in a 25 μl volume of assay buffer (50 mmol/l Tris-HCl, pH 7.75 containing 0.9% (w/v) NaCl, 0.05% (w/v) $NaN_3$, 0.01% (v/v) Tween 40, 0.05% (w/v) bovine-γ-globulin, 20 μmol/l diethylenetriamine-pentaacetate (DTPA) and 0.5% (w/v) BSA). The reactions were incubated for additional 30 min at room temperature with shaking to allow calcium-free forms of calmodulin molecules (indicated with label 3*c* in FIG. 8*b*) to bind (indicated with label 9 in FIG. 8*b*) to antibody-coated nanoparticles and Cy5 fluorescence is measured thereafter in time-resolved mode by Wallac Victor multilabel counter with an excitation filter at 340 nm, an emission filter at 665 nm, 1000 cycles, delay 75 μs and a window 400 μs.

Other Preferred Embodiments

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive ii) a second group comprising a quencher, which quencher is capable of energy transfer from an acceptor, and the first and second group are linked by at least a first linkage, and an increase, of fluorescence of said acceptor, due to the decrease, of energy transfer from said acceptor to said quencher resulting from cleavage of said first linkage, is measured, iii) a third group comprising a donor for energy transfer to said acceptor, which donor is an up-conversion fluorescent compound, a long-lifetime fluorescent compound or an electrogenerated luminescent compound; and wherein a conformational or terminal epitope is created on said first group through said cleavage of the linkage, and said third group comprises a binder with affinity for binding to said conformational or terminal epitope; and wherein fluorescence of said acceptor is brought about by exciting the donor resulting in energy being transferred from the donor to the acceptor, wherein said assay method includes the following steps a) bringing the sample, the first group, the second group and optionally the third group, in contact with each other to obtain an assay mixture, b) allowing the assay mixture to react, c) bringing the third group in contact with the assay mixture if it was not brought in contact with the assay mixture in step a), d) allowing the third group to react with the assay mixture if it was brought in contact with the assay mixture in step c), e) exciting the donor, and f) measuring the sensitized emission of the acceptor.

2. The assay method according to claim 1 characterized in that the quencher is non-luminescent.

3. The assay method according to claim 1 characterized in that the donor is excited either by light or electrochemically.

4. The assay method according to claim 1, characterized in that the first linkage is a covalent linkage.

5. The assay method according to claim 1, characterized in that the first linkage is a non-covalent linkage.

6. The assay method according to claim 4 characterized in that the first group and/or the second groups comprises an oligopeptide, oligonucleotide or oligosaccharide.

---

---

The invention claimed is:

1. A homogenous bioassay method for use in measurement of biological activity, its modulation or analyte concentration of a sample, said bioassay comprising i) a first group comprising an acceptor, which acceptor is a short lifetime fluorescent compound capable of energy transfer, and 7. The assay method according to claim 4, characterized in that cleavage of the first group from the second group is enzymatic.

8. The assay method according to claim 1, characterized in that the first group and the second groups are covalently linked with a further second linkage and the lengthening of the distance between the acceptor and quencher results from cleavage of the first linkage.

9. The assay method according to claim 1, characterized in that the third group is a particulate comprising one or more donors and one or more binders.

10. The assay method according to claim 9 characterized in that the particulate has a diameter of <10 μm.

11. The assay method according to claim 10 characterized in that the particulate has a diameter of <400 nm.

12. The assay method according to claim 11 characterized in that the particulate has a diameter of <100 nm.

13. The assay method according to claim 1, characterized in that the third group is incorporated in a solid-surface or a surface coating comprising one or more donors and one or more binders.

14. A kit for a homogenous bioassay according to claim 1, characterized in that said kit comprises reagents including
   i) a first group comprising an acceptor, which acceptor is a short lifetime fluorescent compound capable of energy transfer, and
   ii) a second group linked to said first group by at least a first linkage, said second group comprising a quencher, which quencher is capable of energy transfer from an acceptor, and
   iii) a third group comprising a donor for energy transfer to said acceptor, which donor is an up-conversion fluorescent compound, a long-lifetime fluorescent compound or an electrogenerated luminescent compound; and
   said first group being such that a conformational or terminal epitope is created on said first group through cleavage of said first linkage and said third group comprising a binder with affinity for binding to said conformational or terminal epitope.

15. The kit according to claim 14 characterized in that the quencher is non-luminescent.

16. The kit according to claim 14 characterized in that the first linkage is a covalent linkage.

17. The kit according to claim 14 characterized in that the first linkage is a non-covalent linkage.

18. The kit according to claim 14, characterized in that the first and second groups are covalently linked with a further second linkage.

19. The kit according to claim 14, characterized in that the first group and/or the second groups comprises an oligopeptide, oligonucleotide or oligosaccharide.

20. The kit according to claim 14, characterized in that the first group and the second group have an affinity towards each other.

21. The kit according to claim 14, characterized in that the third group is a particulate comprising one or more donors and one or more binders.

22. The kit according to claim 21 characterized in that the particulate has a diameter of <10 μm.

23. The kit according to claim 22 characterized in that the particulate has a diameter of <400 nm.

24. The kit according to claim 23 characterized in that the particulate has a diameter of <100 nm.

25. The kit according to claim 14, characterized in that the third group is incorporated in a solid-surface or a surface coating comprising one or more donors and one or more binders.

* * * * *